US012647688B2

(12) United States Patent
Yorozu et al.

(10) Patent No.: US 12,647,688 B2
(45) Date of Patent: Jun. 2, 2026

(54) OBSERVATION SYSTEM AND LIGHT EMITTING METHOD

(71) Applicant: Sony Olympus Medical Solutions Inc., Tokyo (JP)

(72) Inventors: Shutaro Yorozu, Kanagawa (JP); Sadayuki Tamonoki, Tokyo (JP); Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 160 days.

(21) Appl. No.: 18/762,708

(22) Filed: Jul. 3, 2024

(65) Prior Publication Data

US 2025/0024156 A1      Jan. 16, 2025

(30) Foreign Application Priority Data

| Jul. 10, 2023 | (JP) | ................................. | 2023-113310 |
| Mar. 4, 2024 | (JP) | ................................. | 2024-032445 |
| Apr. 23, 2024 | (JP) | ................................. | 2024-070040 |

(51) Int. Cl.
 *A61B 1/04* (2006.01)
 *A61B 1/00* (2006.01)
 (Continued)

(52) U.S. Cl.
 CPC ....... *H04N 23/745* (2023.01); *A61B 1/00009* (2013.01); *A61B 1/0005* (2013.01);
 (Continued)

(58) Field of Classification Search
 CPC ...... H04N 23/745; H04N 23/13; H04N 23/71; H04N 23/74; H04N 23/667;
 (Continued)

(56) References Cited

U.S. PATENT DOCUMENTS

| 2018/0153386 A1* | 6/2018 | Omori | ................... | A61B 1/0005 |
| 2018/0234603 A1* | 8/2018 | Moore | ................... | H04N 23/71 |

(Continued)

FOREIGN PATENT DOCUMENTS

JP        2009-268617 A      11/2009

*Primary Examiner* — Howard D Brown, Jr.
(74) *Attorney, Agent, or Firm* — XSENSUS LLP

(57) ABSTRACT

An aspect of the present disclosure relates to an observation system including a control device that controls irradiation light with which different irradiation environments are irradiated, in which the control device includes a control unit that controls a light source device that generates the irradiation light, and an acquisition unit that acquires irradiation environment information regarding an irradiation environment of the irradiation light, and the control unit causes a display unit to display a first software key in a case where the irradiation environment information acquired by the acquisition unit includes an open field, and causes the display unit to display a second software key in a case where the irradiation environment information does not include an open field, a function corresponding to predetermined light emission is disabled in the first software key, and the function corresponding to the predetermined light emission is enabled in the second software key.

24 Claims, 23 Drawing Sheets

(51) Int. Cl.

| | |
|---|---|
| *A61B 1/06* | (2006.01) |
| *H04N 23/13* | (2023.01) |
| *H04N 23/71* | (2023.01) |
| *H04N 23/74* | (2023.01) |
| *H04N 23/745* | (2023.01) |
| *H04N 23/667* | (2023.01) |

(52) U.S. Cl.

CPC ............ *A61B 1/043* (2013.01); *A61B 1/0653* (2013.01); *A61B 1/0655* (2022.02); *H04N 23/13* (2023.01); *H04N 23/71* (2023.01); *H04N 23/74* (2023.01); *H04N 23/667* (2023.01)

(58) Field of Classification Search

CPC ... A61B 1/00009; A61B 1/0005; A61B 1/043; A61B 1/0653; A61B 1/0655; A61B 1/00006; A61B 1/0638

See application file for complete search history.

(56) References Cited

U.S. PATENT DOCUMENTS

| | | | | |
|---|---|---|---|---|
| 2018/0303321 | A1* | 10/2018 | Takata ................. | G02B 26/127 |
| 2021/0386270 | A1* | 12/2021 | Tanigami ............ | A61B 1/0655 |
| 2022/0210379 | A1* | 6/2022 | Westwick ........... | A61B 5/0071 |
| 2022/0313070 | A1* | 10/2022 | Tatsuta ................ | A61B 1/0623 |
| 2022/0378276 | A1* | 12/2022 | Fujita ........................ | G06T 7/62 |
| 2023/0037060 | A1* | 2/2023 | Shimomura ......... | A61B 1/0653 |
| 2023/0200682 | A1* | 6/2023 | Yoshioka ............. | A61B 5/1076 |
| | | | | 600/593 |
| 2023/0319386 | A1* | 10/2023 | Hayashi ................ | H04N 23/73 |
| | | | | 348/68 |
| 2023/0363630 | A1* | 11/2023 | Hayashi ............ | G02B 19/0066 |
| 2024/0268651 | A1* | 8/2024 | Hayashi ............... | H04N 23/125 |
| 2024/0354943 | A1* | 10/2024 | Ajani ..................... | G06V 10/25 |
| 2025/0213101 | A1* | 7/2025 | Feingold ............... | A61B 1/045 |

* cited by examiner

Figures 10A, 10B, 10C:
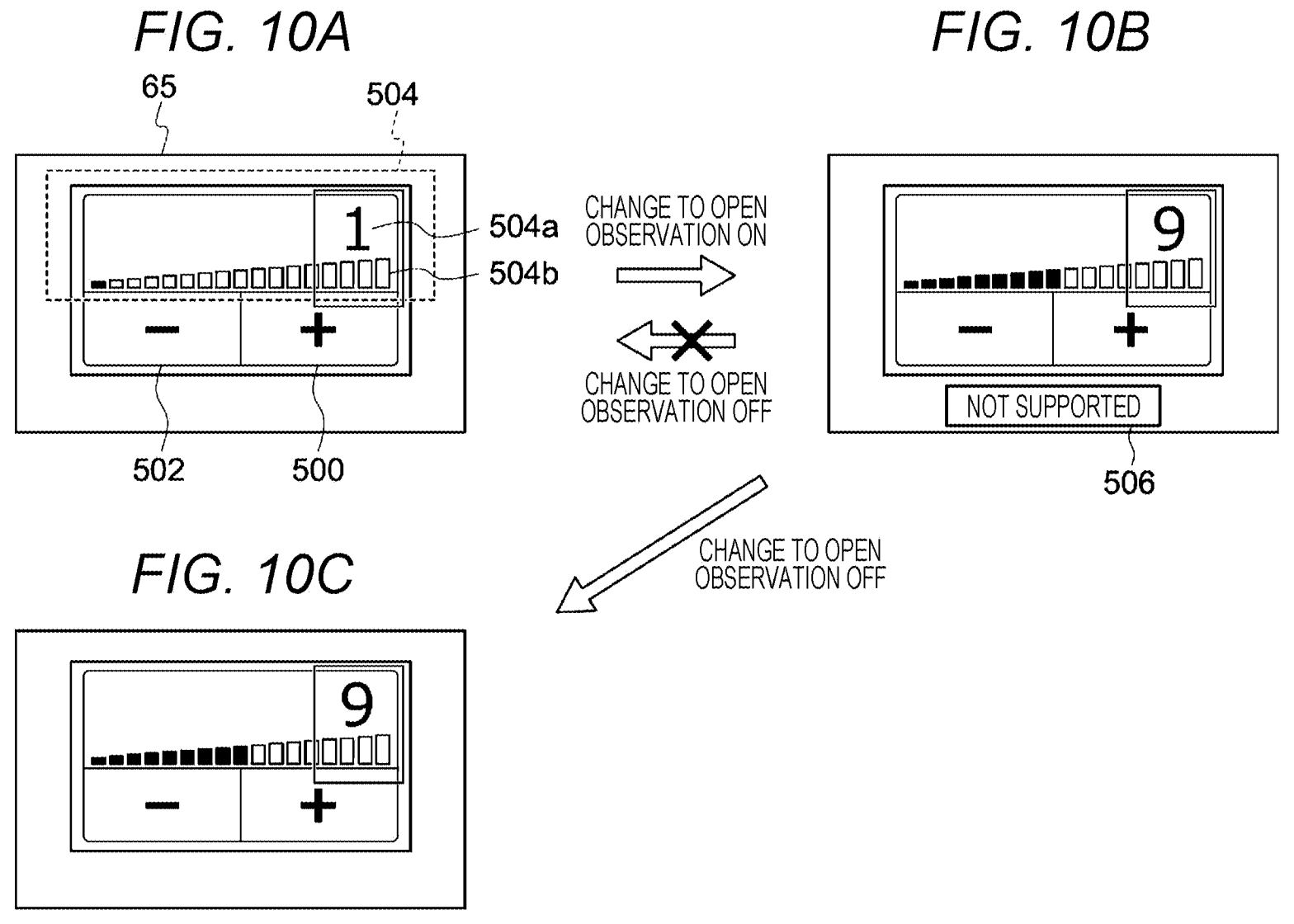

NOT SUPPORTED

CHANGE TO OPEN OBSERVATION ON

CHANGE TO OPEN OBSERVATION OFF

CHANGE TO OPEN OBSERVATION OFF

| DISPLAY INDEX | 1 TO 8 | 9 | 10 | ⋯ | 17 |
|---|---|---|---|---|---|
| SETTING INDEX | 9 | 9 | 10 | ⋯ | 17 |

CHANGE TO OPEN OBSERVATION ON

CHANGE TO OPEN OBSERVATION OFF

| DISPLAY INDEX | 1 | 2 | 3 | 4 ··· | 14 | 15 | 16 | 17 |
|---|---|---|---|---|---|---|---|---|
| SETTING INDEX | 1 | 2 | 3 | 4 ··· | 14 | 15 | 16 | 17 |

CHANGE TO OPEN OBSERVATION ON

CHANGE TO OPEN OBSERVATION OFF

OBSERVATION SYSTEM AND LIGHT EMITTING METHOD

CROSS-REFERENCE TO RELATED APPLICATION

This application claims the benefit of Japanese Priority Patent Application JP 2024-070040 filed Apr. 23, 2024, which claims benefit of Japanese Priority Patent Application JP 2024-032445 filed Mar. 4, 2024, which claims benefit of Japanese Priority Patent Application JP 2023-113310 filed Jul. 10, 2023, the entire contents of each are incorporated herein by reference.

TECHNICAL FIELD

The present disclosure relates to an observation system and a light emitting method.

BACKGROUND ART

It is generally known to shorten a period for storing charges and increase a transfer rate of an image signal when an optical image via an endoscope such as a rigid endoscope is captured by an imaging element. To implement this, there is a case where blinking light is used as illumination light to be supplied from a light source device to the endoscope. Furthermore, in a case where blinking light is used as the illumination light, in a situation where the blinking light enters the eyes of an operator, and the like, a frequency range of the blinking light is switched to a frequency range in which flickering is not felt.

CITATION LIST

Patent Literature

[PTL 1]
    JP 2009-268617 A

SUMMARY

Technical Problem

However, a light source device to be used in an illumination device for image observation such as a rigid endoscope may be provided to be connectable to other medical observation devices. For example, in a case where a laparotomy is performed, a light source device may be connected to a medical illumination device such as a ring light. In this case, a common user interface may be used for light emission control of the light source device between the illumination device for image observation and the medical illumination device.

Furthermore, due to a difference in application, characteristics of the illumination light may be changed between a case where the light source device is connected to the illumination device for image observation and a case where the light source device is connected to the medical illumination device. However, the light source device can be connected to both the illumination device for image observation and the medical illumination device, and thus, the illumination light to be selected may be erroneously selected on a user interface.

The present disclosure provides an observation system and a light emitting method that prevent erroneous selection of illumination light to be used in an illumination device for image observation and illumination light to be used in a medical illumination device.

Solution to Problem

An aspect of the present disclosure relates to an observation system including a control device that controls irradiation light with which different irradiation environments are irradiated, in which the control device includes a control unit that controls a light source device that generates the irradiation light, and an acquisition unit that acquires irradiation environment information regarding an irradiation environment of the irradiation light, the control unit causes a display unit to display a first software key in a case where the irradiation environment information acquired by the acquisition unit includes an open field, and causes the display unit to display a second software key in a case where the irradiation environment information does not include an open field, and a function corresponding to predetermined light emission is disabled in the first software key, and the function corresponding to the predetermined light emission is enabled in the second software key.

The predetermined light emission may be light emission that causes flickering that can be sensed by human eyes. The predetermined light emission may be light emission in which a plurality of light emission states which is different in at least one of brightness or wavelength is temporally switched at a frequency equal to or higher than 3 Hz and less than 65 Hz.

The predetermined light emission may be light emission in which at least a first state and a second state in which light emission intensity in a band of visible light is higher than that in the first state are periodically repeated, and the second state is a period longer than 7.7 ms.

The software key to be disabled and the software key to be enabled may be displayed in different display modes on the display unit.

The first software key and the second software key may be software keys related to brightness control and may be associated with target values of brightness.

A range of brightness selectable by the second software key may be wider than a range of brightness selectable by the first software key.

A range of a target value of brightness selectable by a user may change between the first software key and the second software key.

The first software key and the second software key may be associated with an observation mode selection function.

The first software key and the second software key may be a function for selecting a fluorescence wavelength or excitation wavelength.

A function corresponding to light emission of visible light may be disabled in the first software key, and the function corresponding to the light emission of the visible light is enabled in the second software key.

The acquisition unit may acquire a type of a light guide unit connected to the light source device as the irradiation environment information, may determine that an open field is included in a case where the light source device is connected via a first-type light guide unit, and may determine that the open field is not included in a case where the light source device is connected via a second-type light guide unit different from the first-type light guide unit.

The acquisition unit may acquire a captured image output from an imaging device that captures an image of light from a subject as the irradiation environment information and may determine whether or not the open field is included on the basis of the captured image.

The acquisition unit may have a recognition function of recognizing a category of the captured image, and the acquisition unit may determine whether or not the open field is included on the basis of the category.

An illumination device for image observation in a state of being attached to an imaging device may cause the imaging device to receive light from a subject while shielding part of the light in a form different from that of an illumination device for open field in a state of being attached to the imaging device, and the acquisition unit may acquire information on a light shielding portion in a captured image output from the imaging device as the irradiation environment information, and may determine whether or not the open field is included on the basis of the information on the light shielding portion.

The acquisition unit may acquire information as to whether or not an illumination device for image observation has passed through a trocar as the irradiation environment information and may determine whether or not the open field is included on the basis of the information as to whether or not the illumination device for image observation has passed through the trocar.

The first software key may be displayed on the display unit upon activation of the control device.

The observation system may further include the light source device connectable to an illumination device for image observation and an illumination device for open field, and an imaging device connectable to the illumination device for image observation and the illumination device for open field.

In a case where an imaging device connected to the control device includes a first imaging element that receives white light and a second imaging element that receives fluorescence generated by excitation light, the observation system may have a mode in which the control device executes control of causing the light source device to periodically emit the excitation light and the white light at predetermined intervals and causing the light source device to emit light in at least part of a wavelength band of the white light also during a light emission period of the excitation light.

The predetermined light emission may be light emission that causes flickering that is perceivable by human eyes and light emission that causes flickering that is not perceivable by human eyes but affects humans.

The predetermined light emission is light emission in which a plurality of light emission states which is different in at least one of brightness or a wavelength is temporally switched at a frequency equal to or higher than 3 Hz and less than X Hz which is a predetermined value, and X Hz may be a frequency that can be determined based on a region in which the observation system is to be used.

The predetermined light emission may be light emission in which at least a first state and a second state in which light emission intensity in a band of visible light is higher than that in the first state are periodically repeated, and the second state is maintained for a period longer than Y ms, and Y ms may be a value obtained by dividing 500 by X Hz.

Another aspect of the present disclosure relates to a light emitting method for emitting irradiation light with which different irradiation environments are irradiated, the light emitting method including: acquiring an information signal including irradiation environment information regarding an irradiation environment of the irradiation light; determining whether or not the irradiation environment information includes an open field by the information signal; and causing a display unit to display a first software key by a control signal in a case where the irradiation environment information includes the open field, and causing the display unit to display a second software key by the control signal in a case where the irradiation environment information does not include the open field, in which a function corresponding to predetermined light emission is disabled in the first software key, and the function corresponding to the predetermined light emission is enabled in the second software key.

Another aspect of the present disclosure relates to an observation system including a control device that controls irradiation light with which different irradiation environments are irradiated, in which the control device includes a control unit that controls a light source device that generates the irradiation light, and an acquisition unit that acquires irradiation environment information regarding an irradiation environment of the irradiation light, the control unit causes a display unit to display a first software key in a case where the irradiation environment information acquired by the acquisition unit includes an open field, and causes the display unit to display a second software key in a case where the irradiation environment information does not include an open field, the first software key corresponds to a function of periodically repeating at least a first state and a second state in which light emission intensity in a band of visible light is higher than that in the first state, and has a limitation such that the second state is light emission for a period longer than 7.7 ms, and the second software key does not have the limitation.

BRIEF DESCRIPTION OF DRAWINGS

FIGS. 10A to 10C are views illustrating an aspect in which a display form transitions according to the determination of an acquisition unit.

FIG. 15 is a table indicating target values of brightness associated with software keys.

FIGS. 16A and 16B are views illustrating an aspect in which the determination of the acquisition unit transitions.

FIGS. 23A and 23B are views illustrating an aspect in which the determination of the acquisition unit transitions according to fluorescence imaging.

DESCRIPTION OF EMBODIMENTS

Hereinafter, embodiments of the present disclosure will be described with reference to the drawings.

First Embodiment

Figure 1:
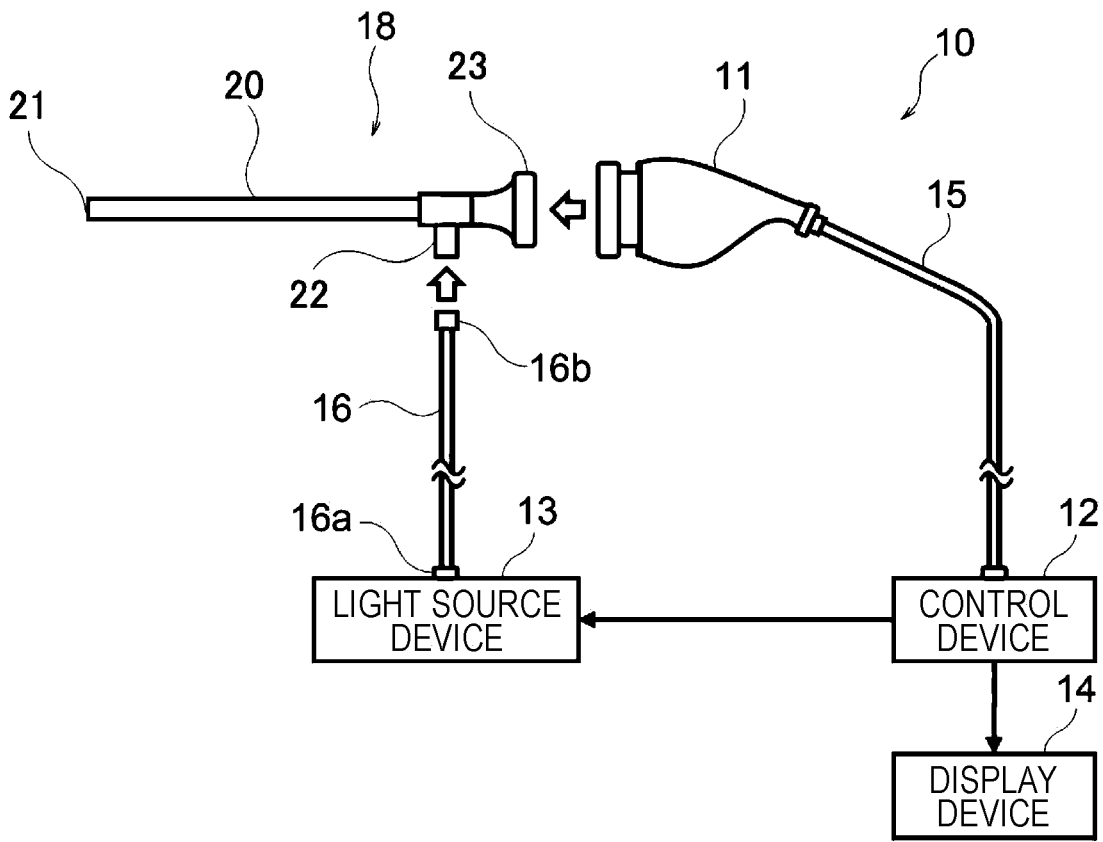
FIG. 1 is a view illustrating an example of a medical observation system and particularly illustrates a case where the medical observation system is configured as an endoscope device including a rigid endoscope (endoscope).
Figure 2:
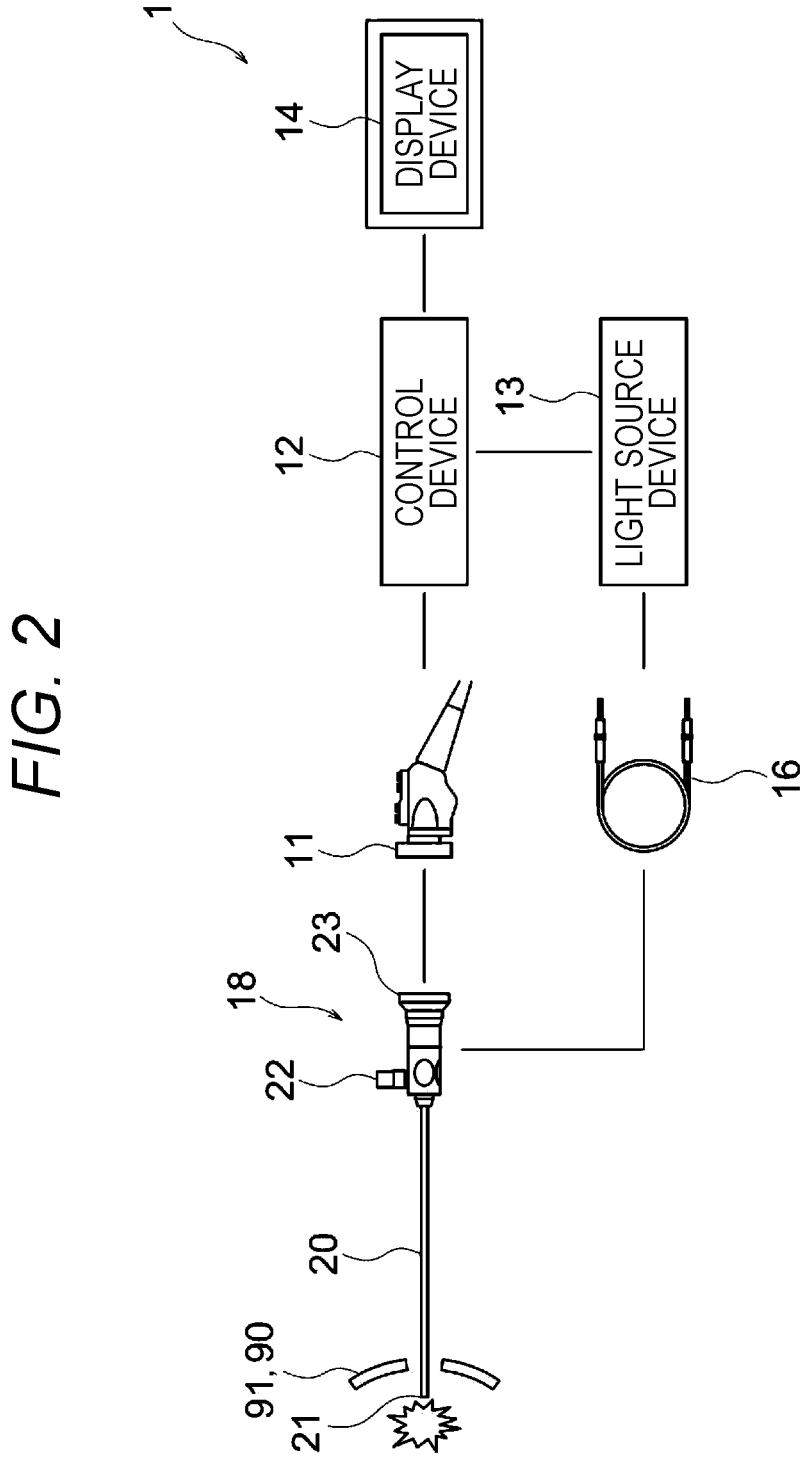
FIG. 2 is a conceptual diagram illustrating a usage example (particularly, an example of light emission from the rigid endoscope) of the medical observation system configured as the endoscope device.

FIG. 1 is a view illustrating an example of an observation system 10 and particularly illustrates a case where a medical observation system is configured as an endoscope device including a rigid endoscope (endoscope: an illumination device for image observation for living body observation) 18. FIG. 2 is a conceptual diagram illustrating a usage example (particularly, an example of light emission from the rigid endoscope 18) of the observation system 10 configured as the endoscope device.

Figure 3:
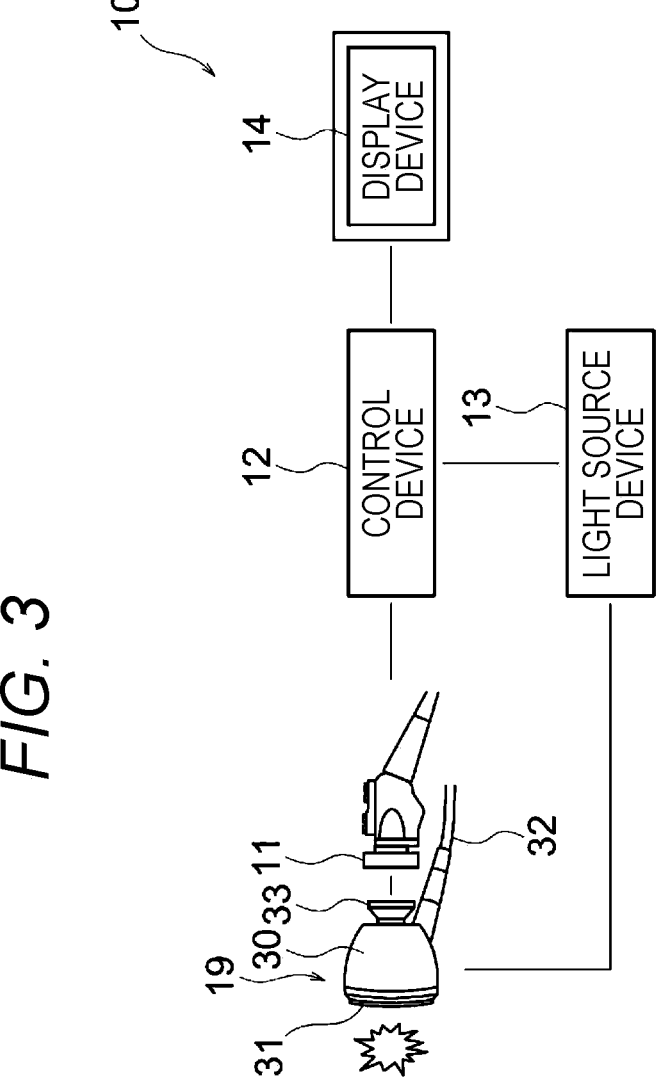
FIG. 3 is a conceptual diagram illustrating a usage example (particularly, an example of light emission from a ring light) of a medical observation system configured as an operative field illumination observation device in which the ring light (medical illumination device) is connected to a light source device.

FIG. 3 is a conceptual diagram illustrating a usage example (particularly, an example of light emission from a ring light 19) of the observation system 10 configured as an operative field illumination observation device in which the ring light (illumination device for open field for living body observation) 19 is connected to a light source device 13.

The observation system 10 is used to observe a target site of a subject 90 such as a patient via a captured image or to observe the target site with the naked eye. The observation system 10 illustrated in FIG. 1 includes an imaging device 11, a control device 12, the light source device 13, and a display device 14.

The light source device 13 is provided to be connectable to the rigid endoscope 18 (see FIGS. 1 and 2) and the ring light 19 (see FIG. 3) and emits light under control of the control device 12. The light source device 13 can emit light in an arbitrary wavelength range and can have an arbitrary device configuration capable of emitting white light and/or narrow band light, for example.

The white light referred to herein is light containing visible light components of various colors, and specific spectral characteristics (wavelength distribution) are not limited as long as the white light can be perceived as white. On the other hand, the narrow band light includes light in a specific wavelength region among a visible light wavelength region and an invisible light wavelength region as main light components and has arbitrary spectral characteristics based on a center wavelength (peak wavelength). The light source device 13 may emit, as narrow band light, excitation light (for example, infrared light) for exciting a fluorescent staining reagent to be used for staining a tissue (cell) to be observed to emit fluorescence, for example.

Note that the light source device 13 may be configured to be able to emit not only light for irradiating an observation target but also light for other arbitrary purposes (for example, light for confirming a connection state between the light guide 16 and the rigid endoscope 18) as necessary.

The rigid endoscope 18 of the present example is connected to the light source device 13 via a detachable light guide 16 (first-type light guide unit). In other words, a first light guide end portion 16a on one end side of the light guide 16 is detachably attached to the light source device 13, and a second light guide end portion 16b on the other end side is detachably connected to an optical connection portion 22 of the rigid endoscope 18.

On the other hand, the ring light 19 (see FIG. 3) of the present example includes a light guide 32 (second-type light guide unit) as part of the ring light 19 and is connected to the light source device 13 via the light guide 32. In other words, one end portion of the light guide 32 is provided integrally with a main body portion 30 of the ring light 19 (that is, so as not to be detached from the main body portion 30), and the other end portion of the light guide 32 is detachably connected to the light source device 13.

The rigid endoscope 18 illustrated in FIGS. 1 and 2 includes an insertion portion 20, and the optical connection portion 22 and an imaging connection portion 23 provided on a proximal end side of the insertion portion 20. A light transmission unit (light guide) and an objective lens are provided on an end surface of an insertion distal end portion 21 of the insertion portion 20 located on the side opposite to the proximal end side.

Light sent from the light source device 13 via the light guide 16 is emitted from the light transmission unit of an end surface on a distal end side of the insertion portion 20, and its reflected light (observation light/imaging light) enters the objective lens and is guided to the imaging connection portion 23 through inside of the insertion portion 20.

The imaging connection portion 23 is detachably connected to a connection portion of the imaging device 11. The observation light sent through the objective lens is incident on the imaging device 11 through the imaging connection portion 23 and received by the imaging device 11. The imaging connection portion 23 can also function as an eyepiece unit. In a state where the imaging connection portion 23 is detached from the imaging device 11, a user such as an operator can directly view the observation light via the imaging connection portion 23.

On the other hand, the ring light 19 illustrated in FIG. 3 includes the main body portion 30, a light emitting unit 31 provided integrally with the main body portion 30, the light guide 32, and an imaging connection portion 33. The light sent from the light source device 13 via the light guide 32 is emitted from the light emitting unit 31, and the reflected light (observation light/imaging light) is guided to the imaging connection portion 33 via an optical system (not illustrated) provided inside the main body portion 30.

The imaging connection portion 33 is detachably connected to the connection portion of the imaging device 11, and the observation light sent via the optical system enters the imaging device 11 through the imaging connection portion 33 and is received by the imaging device 11. The imaging connection portion 33 can also function as an eyepiece unit. In a state where the imaging connection portion 33 is detached from the imaging device 11, a user such as an operator can directly view the observation light via the imaging connection portion 33.

The imaging device 11 is provided to be connectable to the rigid endoscope 18 and the ring light 19 and receives the observation light via the rigid endoscope 18 or the ring light 19 connected thereto. The imaging device 11 is connected to the control device 12 via a signal transmission cable 15 (see FIG. 1; not illustrated in FIGS. 2 and 3). A captured image corresponding to the observation light received via the rigid endoscope 18 or the ring light 19 is transmitted from the imaging device 11 to the control device 12 via the signal transmission cable 15.

The control device 12 is connected to the imaging device 11, the light source device 13, and the display device 14 and controls the imaging device 11, the light source device 13, and the display device 14. Furthermore, the control device 12 can also control the rigid endoscope 18 or the ring light 19 connected to the imaging device 11 via the imaging device 11. For example, the control device 12 causes the display device 14 to display the captured image transmitted from the imaging device 11 or controls light emission of the light source device 13 as described later.

In a case where the rigid endoscope 18 is used in the above-described observation system 10 (see FIG. 2), for example, the insertion distal end portion 21 of the rigid endoscope 18 is inserted into the abdominal cavity (body) inside a peritoneum 91 of the subject 90, and light is emitted from the insertion distal end portion 21 in the abdominal cavity. On the other hand, in a case where the ring light 19 is used (see FIG. 3), the ring light 19 emits light from the light emitting unit 31 outside the subject 90 (peritoneum 91).

Next, a functional configuration example of the observation system 10 will be described.

Figure 4:
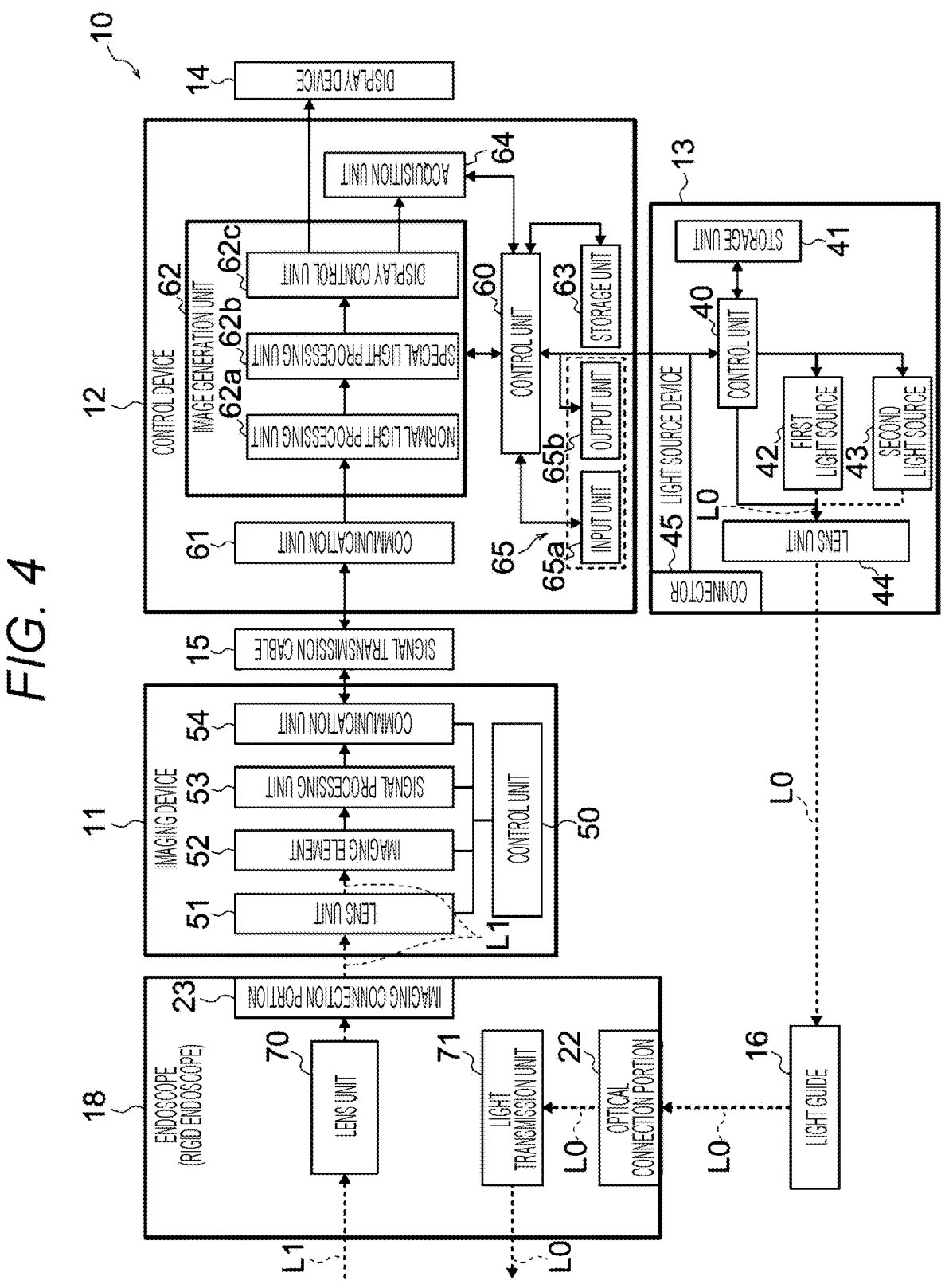
FIG. 4 is a block diagram illustrating a functional configuration example of the medical observation system (endoscope device) including the rigid endoscope.

FIG. 4 is a block diagram illustrating a functional configuration example of the medical observation system (endoscope device) 10 including the rigid endoscope 18.

Figure 5:
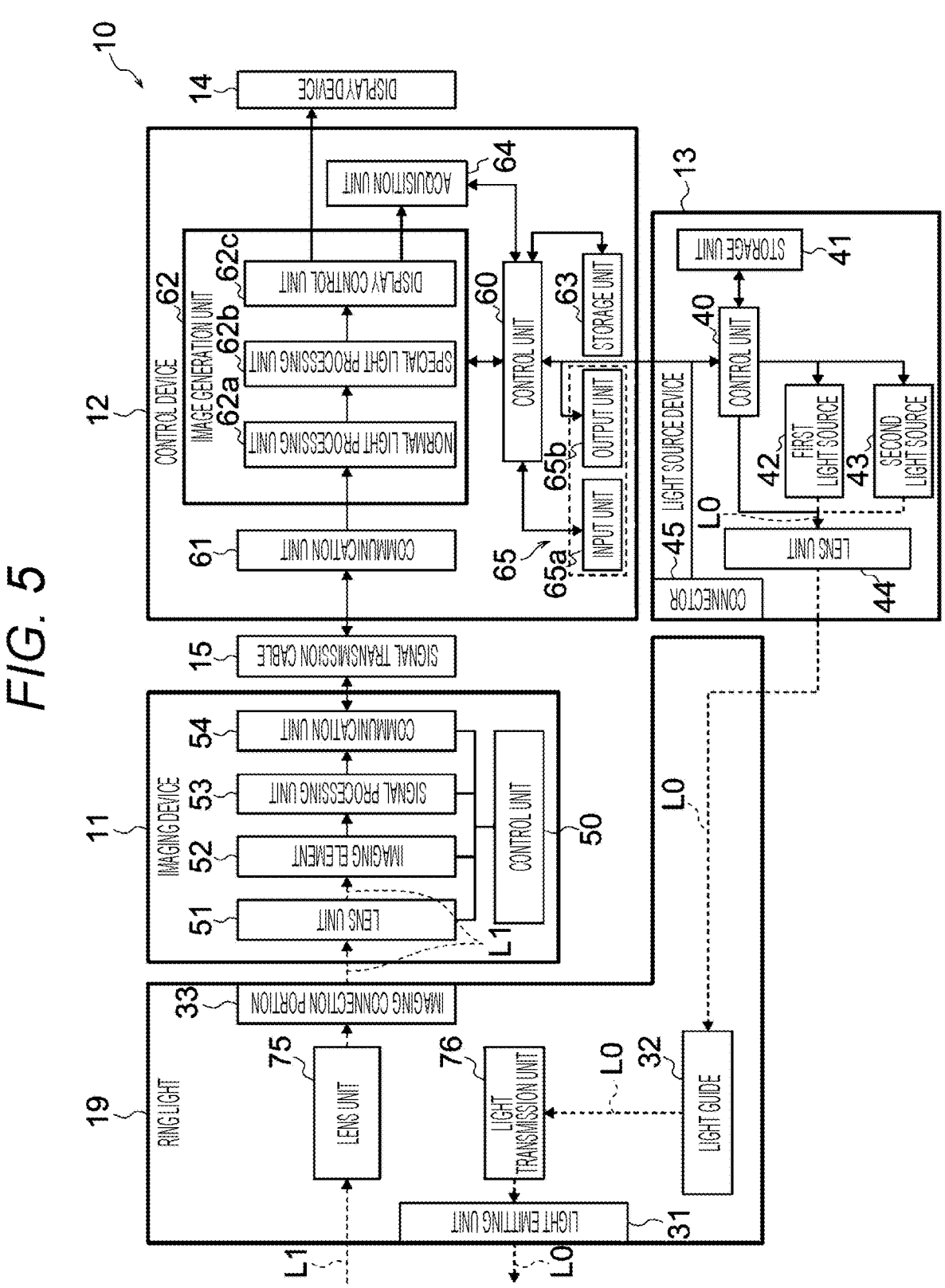
FIG. 5 is a block diagram illustrating a functional configuration example of the medical observation system (operative field illumination observation device) including the ring light.

FIG. 5 is a block diagram illustrating a functional configuration example of the medical observation system (operative field illumination observation device) 10 including the ring light 19.

In the observation system 10 (the endoscope device and the operative field illumination observation device) illustrated in FIGS. 4 and 5, the imaging device 11, the control device 12, and the light source device 13 have the same configuration. In other words, the observation system 10 constitutes the endoscope device (see FIG. 4) by connecting the rigid endoscope 18 to the imaging device 11 and the light source device 13 and constitutes the operative field illumination observation device (see FIG. 5) by connecting the ring light 19 to the imaging device 11 and the light source device 13.

The light source device 13 illustrated in FIGS. 4 and 5 includes a control unit 40, a storage unit 41, a first light source 42, a second light source 43, a lens unit 44, and a connector 45.

The control unit 40 of the light source device 13 controls the first light source 42, the second light source 43, and the lens unit 44 under control of the control device 12 (particularly, the control unit 60).

In the present example, the first light source 42 emits white light, and the second light source 43 emits narrow band light. The light emitted by the first light source 42 and the second light source 43 travels through the lens unit 44 toward the light guide 16 (see FIG. 4)/light guide 32 (see FIG. 5) connected to the connector 45.

Note that emission of the white light from the first light source 42 and emission of the narrow band light from the second light source 43 may be performed simultaneously, alternately, or only one of them may be performed. Furthermore, the control unit 40 accesses the storage unit 41 as necessary, reads out information (which may include data and a program) from the storage unit 41 and stores new information in the storage unit 41.

The imaging device 11 illustrated in FIGS. 4 and 5 includes a control unit 50, a lens unit 51, an imaging element 52, a signal processing unit 53, and a communication unit 54. Observation light (imaging light) L1 incident on the imaging device 11 is guided by the lens unit 51 and received by the imaging element 52. The imaging element 52 includes, for example, a complementary metal-oxide-semiconductor (CMOS) image sensor or a charge-coupled device (CCD) image sensor. A captured image output from the imaging element 52 that has received the observation light L1 is subjected to image processing (signal processing) in the signal processing unit 53, and then transmitted to the control device 12 via the communication unit 54.

The lens unit 51, the imaging element 52, the signal processing unit 53, and the communication unit 54 are driven under control of the control unit 50. The control unit 50 of the imaging device 11 is controlled by the control device 12 (particularly, the control unit 60).

The control device 12 illustrated in FIGS. 4 and 5 includes a control unit 60, a communication unit 61, an image generation unit 62, a storage unit 63, an acquisition unit 64, and a touch panel 65. Furthermore, the touch panel 65 includes an input unit 65*a* and an output unit 66*b*. Note that the touch panel 65 according to the present embodiment corresponds to a display unit.

The captured image received from the communication unit 54 of the imaging device 11 via the signal transmission cable 15 and the communication unit 61 is subjected to various kinds of processing in the image generation unit 62. For example, in a case where the captured image is a normal image based on white light, the captured image is subjected to arbitrary image processing by a normal light processing unit 62*a* of the image generation unit 62, then processed into a display image by a display control unit 62*c*, and the display image is output to the display device 14 and the acquisition unit 64. Furthermore, in a case where the captured image is an excitation light emission image (fluorescence image) of a fluorescent staining reagent, the captured image is subjected to arbitrary image processing by a special light processing unit 62*b* of the image generation unit 62, and then processed into a display image by the display control unit 62*c*, and the display image is output to the display device 14 and the acquisition unit 64. The display device 14 displays the display image received from the image generation unit 62. Data to be used and/or generated by the image generation unit 62 (each of the normal light processing unit 62*a* to the display control unit 62*c*) is transmitted to the control unit 60 as necessary.

The control unit 60 controls the image generation unit 62, the storage unit 63, the acquisition unit 64, and the touch panel 65. Furthermore, the control unit 60 accesses the storage unit 63 as necessary, reads out information (which can include data and a program) from the storage unit 63 and stores new information in the storage unit 63. The acquisition unit 64 acquires an information signal including irradiation environment information regarding an irradiation environment. In other words, the acquisition unit 64 can determine whether or not the irradiation environment information includes an open field. For example, the acquisition unit 64 determines whether or not the irradiation environment information, which is information on the irradiation environment on which either the rigid endoscope 18 connected to the light source device 13 or the ring light 19 performs irradiation, includes an open field. This enables the acquisition unit 64 to determine whether a medical illumination device connected to the light source device 13 is in the irradiation environment of at least one of the rigid endoscope 18 or the ring light 19. Note that the acquisition unit 64 according to the present embodiment has a determination processing function, but is not limited thereto. For example, the control unit 60 may have a determination processing function. Furthermore, details of the acquisition unit 64 will be described later.

Figure 6:
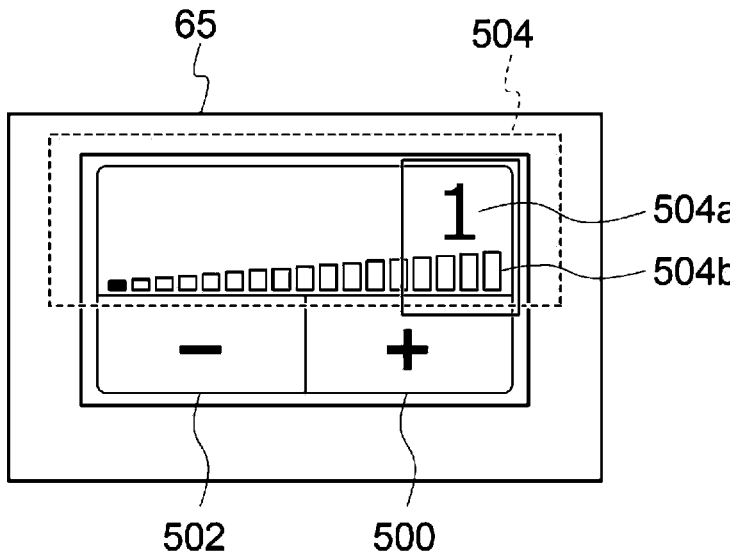
FIG. 6 is a view illustrating an example where a touch panel is constituted with a liquid crystal touch panel.

FIG. 6 is a view illustrating an example in which the touch panel 65 according to the present embodiment is constituted with, for example, a liquid crystal touch panel. The touch panel 65 includes an input unit 65*a* and an output unit 65*b*. For example, software keys 500 and 502 correspond to the input unit 65*a*, and a region 504 corresponds to the output unit 65*b*. For example, an instruction and information input by the user via the input unit 65*a* are transmitted to the control unit 60 and are appropriately used for control by the control unit 60. Furthermore, the output unit 65*b* is driven under control of the control unit 60 and outputs visual information (display information) so as to present various kinds of information to the user.

FIG. 6 illustrates an example of the software keys 500 and 502 for rigid endoscope 18 in a case where the acquisition unit 64 determines that the irradiation environment information does not include an open field. For example, the software keys 500 and 502 are input devices (keys) generated on a screen of the touch panel 65 in a software manner using a control signal under the control unit 60. The software keys 500 and 502 are displayed on the screen of the touch panel 65, and input is performed by specifying a key on the screen. For example, the software keys 500 and 502 are software keys related to brightness control and are associated with target values of brightness. As described above, the software keys 500 and 502 are regions as the input unit 65*a*.

As described above, the region 504 is a region as the output unit 65*b* that presents the visual information (display information) to the user. A target value of brightness is associated with a numerical value 504*a* in the region 504. A display form 504*b* displays a display form corresponding to the numerical value 504*a*. For example, in the display form 504*b*, a light emitting region is increased as the numerical value 504*a* increases.

In the software keys 500 and 502 for rigid endoscope 18, a numerical value as an index can be changed from 1 to 17, for example. As described later, for example, the index from 1 to 8 is a range of light emission that cause flickering that can be sensed by human eyes. More specifically, the index from 1 to 8 is a range in which a first light emission state and a second light emission state in which light emission intensity in a band of visible light is higher than that in the first state are periodically repeated at a frequency of 50 to 60 HZ, for example. Note that the software keys 500 and 502 for rigid endoscope 18 according to the present embodiment correspond to the second software key. Furthermore, the range of light emission that causes flickering that can be sensed by human eyes is, for example, light emission in which a light emission state is temporally switched among a plurality of light emission states which is different in at least one of brightness or wavelength at a frequency equal to or higher than 3 Hz and less than 65 Hz. Furthermore, in the range of light emission that causes flickering that can be sensed by human eyes, at least the first state or the second state in which the light emission intensity in the band of visible light is higher than that in the first state is periodically repeated, and the second state is a period longer than 7.7 ms. In other words, the second state is maintained for a period longer than 7.7 ms. Furthermore, the first state and the second state include both a case where a state is switched between a state in which white light is emitted and a state in which white light is turned off and a case where a state is switched between a state in which brightness of white light is made higher and a state in which brightness of white light is made lower. Furthermore, the first state and the second state include a case where a state is switched between a state in which white light is emitted and a state in which part of a wavelength of the white light does not exist or an output of the part of the white light is very low.

If the software key 500 is instructed, the numerical value 504*a* associated with the target value of brightness increases to, for example, 17. On the other hand, if the software key 502 is instructed, the numerical value 504*a* associated with the target value of brightness decreases to 1. In this event, also in the display form 504*b*, the light emitting region changes in accordance with increase or decrease of the numerical value 504*a*. In this manner, the software keys 500 and 502 are software keys related to brightness control and are associated with target values of brightness.

Figure 7:
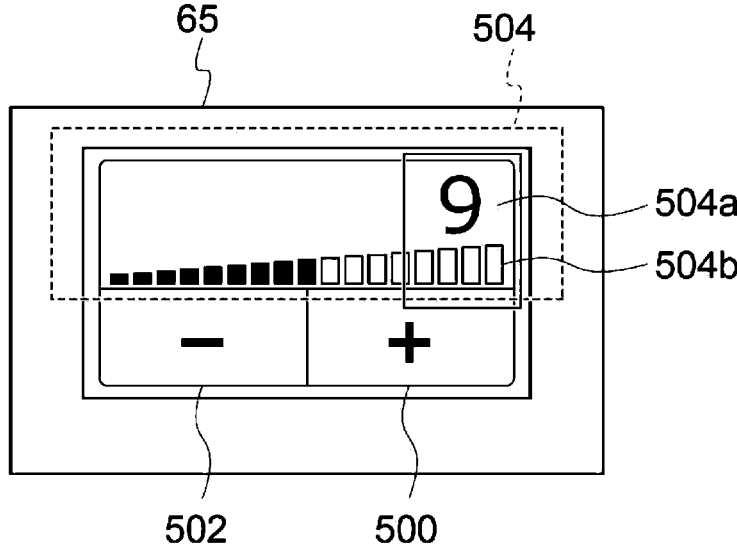
FIG. 7 is a view illustrating an example of a software key for ring light.

FIG. 7 is a view illustrating an example of the software keys 500 and 502 for ring light 19 in a case where the acquisition unit 64 determines that the irradiation environment information includes an open field. In the software keys 500 and 502 for ring light 19, a numerical value that is an index can be changed from 9 to 17, for example. In other words, in the software keys 500 and 502 for ring light 19, a function corresponding to predetermined light emission corresponding to the numerical value from 1 to 8 that is the index is disabled, and in the software keys 500 and 502 for rigid endoscope 18, a function corresponding to predetermined light emission corresponding to the numerical value from 1 to 8 that is the index is enabled. The function corresponding to the predetermined light emission is a range of light emission that causes flickering that can be sensed by human eyes. Note that the software keys 500 and 502 for ring light 19 according to the present embodiment correspond to a first software key. As described above, a range of the target value of brightness selectable by the user changes between the software keys 500 and 502 for rigid endoscope 18 and the software keys 500 and 502 for ring light 19. In other words, a range of brightness selectable by the software keys 500 and 502 for ring light 19 is narrower than a range of brightness selectable by the software keys 500 and 502 for rigid endoscope 18. In other words, the range of brightness selectable by the software keys 500 and 502 for rigid endoscope 18 is wider than the range of brightness selectable by the software keys 500 and 502 for ring light 19.

Furthermore, as will be described later, the control unit 60 can control the light source device 13 (control unit 40) according to an instruction via the software keys 500 and 502 to perform light emission control of the light source device 13. Furthermore, although not illustrated, the control unit 60 may control the communication unit 61 and other devices.

The rigid endoscope 18 illustrated in FIG. 4 includes a lens unit 70 and a light transmission unit (light guide) 71 in addition to the optical connection portion 22 and the imaging connection portion 23 described above.

Illumination light L0 (white light and/or narrow band light) sent from the light source device 13 via the light guide 16 passes through the optical connection portion 22, is guided by the light transmission unit 71, and is emitted from an end surface of the insertion distal end portion 21 (see FIG. 2) of the insertion portion 20. On the other hand, the observation light L1 that is reflected light from an observation target and enters the rigid endoscope 18 is guided by the lens unit 70, passes through the imaging connection portion 23, is then guided by the lens unit 51 of the imaging device 11, and is received by the imaging element 52.

On the other hand, the ring light 19 illustrated in FIG. 5 includes a lens unit 75 and a light transmission unit (light guide) 76 in addition to the light emitting unit 31, the light guide 32, and the imaging connection portion 33 described above. The illumination light L0 (white light and/or narrow band light) sent from the light source device 13 via the light guide 32 is guided by the light transmission unit 76 and emitted from the light emitting unit 31. On the other hand, the observation light L1 reflected from the observation target and incident on the ring light 19 is guided by the lens unit 75, passes through the imaging connection portion 33, is then guided by the lens unit 51 of the imaging device 11, and is received by the imaging element 52.

[Light Emission Control of Light Source Device]

As described above, the control device 12 includes the control unit 60 that controls light emission of the light source device 13 connectable to the rigid endoscope 18 and the ring light 19. The control unit 60 controls light emission of the light source device 13 in a first mode (closed field mode) in a case of an image observation mode in which image observation is performed, and controls light emission of the light source device 13 in a second mode different from the first mode in a case of a visual observation mode in which visual observation is performed. In other words, the software keys 500 and 502 for rigid endoscope 18 are used in the first mode (see FIG. 6), and the software keys 500 and 502 for ring light 19 are used in the second mode (open field mode) (see FIG. 7).

Referring again to FIGS. 2 and 3, in the present embodiment, the rigid endoscope (rigid endoscope) 18 is used as an endoscope, but an illumination device that emits light in the body such as a flexible endoscope (flexible endoscope) or other illumination devices for image observation may be used instead. The illumination device for image observation described herein is mainly intended to cause the imaging device 11 to receive light from the subject 90 (subject) that is the observation target and cause the imaging device 11 to output an image for observation of the subject 90.

Furthermore, in the above-described embodiment, the ring light 19 is used as the medical illumination device, but any other illumination device that emits light outside the body of the subject 90 or other illumination devices for open field (for example, a laparotomy light, an operative field light, an endoscope illumination device, a microscope illumination device, an open surgery illumination device, and the like) may be used instead. The illumination device for open field referred to herein may be, for example, an illumination device that can be used to illuminate a desired region (field of view) under an open (opened) environment without progress of light between an observer (particularly eyes) and the subject 90 (observation target) being blocked, and is an illumination device that can be used at least in a case where the subject 90 is viewed by direct view. As described above, the illumination device for open field can be used as an illumination device in a case where observation involving viewing light from at least the subject 90 with the naked eye (observation of the observation target by direct view) is performed. The illumination device for open field can also be used in combination with image observation and can also be used as an illumination device in a case where light from the subject 90 is received by the imaging device 11 and the observation target (subject) is observed by an image.

As described above, the imaging connection portion 23 of the rigid endoscope (endoscope) 18 functions as a connection portion to which the imaging device 11 that captures an image of the observation target is connected, and also functions as an eyepiece (eyepiece) that allows the user to observe the observation target with the naked eye. Thus, the rigid endoscope 18 can function as an illumination device for image observation in a case where the imaging device 11 is connected and can function as an illumination device for open field in a case where the imaging device 11 is not connected.

Thus, in a case where the light source device 13 is connected to the rigid endoscope 18 for image observation, the control unit 60 controls light emission of the light source device 13 in a first mode that is an observation mode mainly based on a captured image, and in a case where the light source device 13 is connected to the ring light 19, the control unit 60 controls light emission of the light source device 13 in a second mode that is an observation mode mainly based on direct view. In a "light emitting method including performing light emission of the light source device 13" to be performed under the control of the control unit 60 of the control device 12 in this manner, in a case where the light source device 13 is connected to the illumination device for image observation (rigid endoscope 18), light emission of the light source device 13 is performed in the first mode. On the other hand, in a case where the light source device 13 is connected to an illumination device for visual observation (for example, in a case where the ring light 19 is used for observation by direct view, and the like), light emission of the light source device 13 is performed in the second mode.

More specifically, the control device 12 (particularly, the control unit 60) that controls light emission of the light source device 13 makes a range of light amount adjustment of the illumination light L0 sent from the light source device 13 to the ring light 19 different from a range of light amount adjustment sent from the light source device 13 to the rigid endoscope 18. Thus, in the ring light 19, the illumination light L0 having frequency characteristics optimized for the rigid endoscope 18 can be supplied from the light source device 13 to the rigid endoscope 18 without the illumination light L0 that causes flickering that can be sensed by human eyes being supplied from the light source device 13. Note that an illumination device for open field such as the ring light 19 may be used for observation with a captured image, for example, in a situation where the illumination light L0 does not directly enter the eyes of the operator, or the like. In such a case, a wavelength component, a cycle, and the like, of light emitted by the light source device 13 can be made different from those in the second mode in accordance with an observation purpose of the image.

A specific example of the light emission adjustment of the light source device 13 will be described later (see FIGS. 8A to 9B).

[Adjustment of Light Emission Intensity]

Regarding the illumination light L0 (visible light (white light)) sent from the light source device 13 to the rigid endoscope 18, light emission intensity (light emission amount) of the illumination light L0 in the light source device 13 may be manually adjusted by the operator (user) via the software keys 500 and 502 or may be automatically adjusted. On the other hand, regarding the illumination light L0 sent from the light source device 13 to the ring light 19, light emission intensity (light emission amount) of the illumination light L0 in the light source device 13 is preferably manually adjusted by the operator (user) via the software keys 500 and 502 (see FIG. 6). Basically, no or almost no ambient light enters the body (abdominal cavity). Thus, in a case where an image of an observation site in the body (abdominal cavity) is captured via the rigid endoscope 18, only reflected light of the illumination light L0 (white light) emitted from the rigid endoscope 18 is substantially received by the imaging device 11, and thus, it is possible to stably and appropriately perform automatic dimming on the basis of the captured image.

On the other hand, in a case where an image of the outside of the body (exposure observation site) is captured via the ring light 19, the observation site can be irregularly irradiated with ambient light whose intensity is not constant, and thus, it is difficult to stably and appropriately perform automatic dimming on the basis of the captured image. Thus, in a case where the illumination light L0 is emitted from the ring light 19, in order to irradiate the observation target with the illumination light L0 having appropriate intensity (brightness), the light emission intensity of the illumination light L0 in the light source device 13 is preferably adjusted manually via the software keys 500 and 502 (see FIG. 7).

As described above, in the first mode in which the illumination light L0 is sent from the light source device 13 to the rigid endoscope 18, the control device 12 may automatically adjust intensity of the light emitted from the light source device 13 on the basis of the captured image acquired by the imaging device 11 connected to the rigid endoscope 18. However, even in such a case, the control device 12 preferably controls the light source device 13 such that the intensity of the light emitted from the light source device 13 is manually adjusted in the second mode in which the light is sent from the light source device 13 to the ring light 19.

In a case where the illumination light L0 is excitation light (narrow band light) for exciting a phosphor (fluorescent staining reagent), it is preferable that the intensity of light emitted by the light source device 13 is basically manually adjusted by the operator (user) via the software keys 500 and 502 (see FIG. 6). A specific tissue stained with a fluorescent staining reagent is not necessarily present in the observation target site, and an amount of fluorescence emission is not necessarily constant depending on a state of the observation target site. Thus, it is difficult to stably and appropriately adjust intensity (light amount) of the excitation light (narrow band light) on the basis of the captured image (fluorescence image) acquired by the imaging device 11, and it is desirable to manually adjust the intensity (light amount).

In a case where visible light is sent from the light source device 13 to the ring light 19, the visible light may include white light or may include narrow band light having a center wavelength included in a visible light wavelength range. In other words, even if the illumination light L0 emitted from the ring light 19 is either white light or narrow band light (visible light), flickering can be reduced by adjusting a light emission frequency as described above.

Here, a specific example of light emission adjustment of the light source device 13 will be described. The example of light emission adjustment described below is implemented by the control device 12 (particularly, the control unit 60) appropriately controlling the light source device 13 (particularly, the control unit 40).

[First Light Emission Adjustment Example]

Figures 8A, 8B:
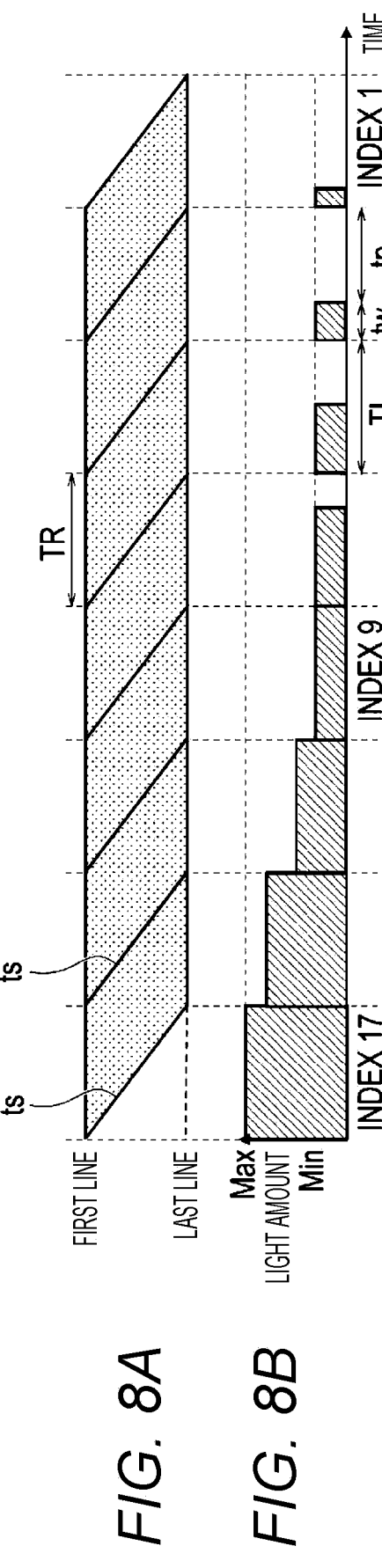
FIGS. 8A and 8B are views illustrating a light emission adjustment example from a case where a target light amount of light emission is maximum to a case where the target light amount of light emission is minimum.
Figures 9A, 9B:
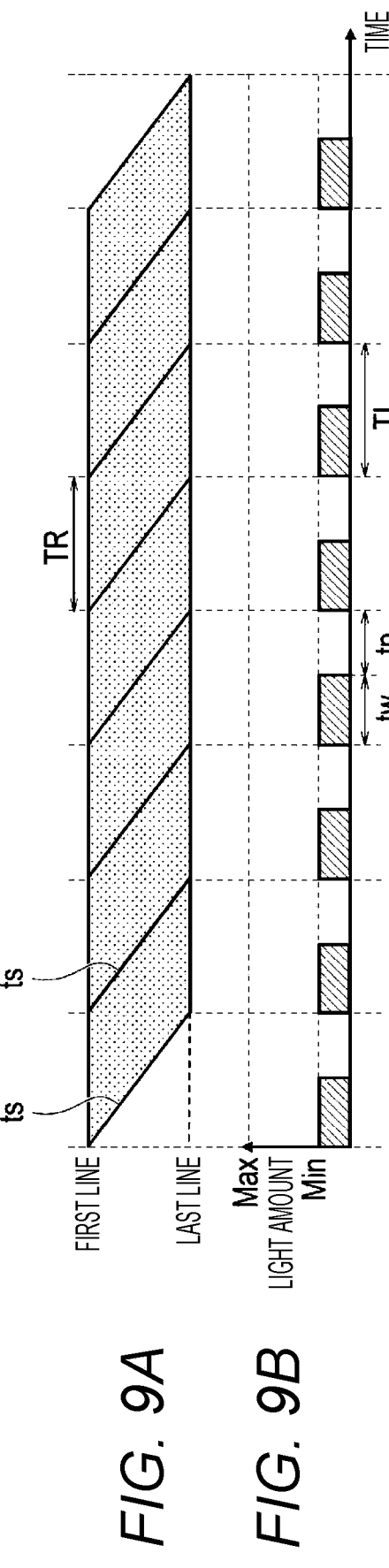
FIGS. 9A and 9B are views for explaining PWM control according to a first light emission adjustment example.

FIGS. 8A to 9B illustrate a case where light (for example, white light) is supplied from the light source device 13 to the rigid endoscope 18. FIGS. 8A and 8B are views illustrating a first light emission adjustment example from a case where a target light amount of light emission of the light source device 13 is maximum (INDEX 17) to a case where the target light amount is minimum (INDEX 1). FIGS. 9A and 9B are views illustrating PWM control (INDEX 5) in the first light emission adjustment example.

FIGS. 8A and 9A illustrate an exposure state of the imaging element 52 (see FIGS. 4 and 5), indicates a horizontal line of the imaging element 52 on a vertical axis, and indicates time on a horizontal axis. In FIGS. 8A and 9A, an uppermost line represents an uppermost horizontal line (that is, a first line), and a lowermost line represents a lowermost horizontal line (that is, a last line). A line (oblique line) indicated by a reference sign "ts" indicates a pixel data reading start timing of each horizontal line regarding each captured image.

FIGS. 8B and 9B illustrate a light emission timing and a light amount of the light source (the first light source 42 and/or the second light source 43 (see FIGS. 4 and 5)). FIGS. 8B and 9B indicate the light emission amount of the light source (that is, the intensity of the illumination light L0 sent from the light source device 13 to the rigid endoscope 18 or the ring light 19) on a vertical axis. FIGS. 8B and 9B indicate time on a horizontal axis, that is, indicates a continuous light emission period (that is, a light emission period of one pulse), and eventually indicates an applied pulse (current drive pulse) of a current to be supplied to the light source.

Note that a value m of "INDEX" (where "m" is an integer from 1 to 17) represents a degree of a target light amount of light emission of the light source device 13, and as "m" is greater (closer to "17"), the target light amount becomes larger, and as "m" is smaller (closer to "1"), the target light amount becomes smaller. Furthermore, "TR" indicates an exposure cycle of each horizontal line of the imaging element 52, and "TL" indicates a light emission cycle of the light source device 13. Furthermore, "tw" indicates a pulse width of light emission of the light source device 13 (that is, a pulse width of a current drive pulse to be supplied to the light source device 13). Furthermore, "tp" indicates an interval between adjacent light emission pulses of the light source device 13 (that is, a time interval between adjacent drive pulses of the current to be supplied to the light source device 13). In a case where the light emission frequency of pulse modulation control is 50 Hz or 60 Hz, flickering may be felt by human eyes. In other words, in a case where the value m of "INDEX" is from 1 to 8, there is a possibility that flickering is felt in a case where light emission of the light source device 13 is directly or indirectly viewed with the naked eye.

<Light Emission Control for Rigid Endoscope>

In a case where the target light emission amount of the light source device 13 is relatively large (for example, in a case of INDEX from "17" to "9"), a current value (magnitude of a current) to be supplied to the light source is adjusted, and the amount of light emission from the light source is adjusted. In other words, while the target light emission amount is relatively large, as the target light emission amount of the light source device 13 decreases, the amount of light emission from the light source itself gradually decreases from a maximum light amount (Max) toward a minimum light amount (Min) (see FIG. 8B).

On the other hand, in a case where the target light emission amount of the light source device 13 is relatively small (for example, in a case of INDEX from "8" to "1"), the amount of light emission from the light source is adjusted by pulse modulation control of a current drive pulse to be supplied to the light source. Specifically, in a state where the amount of light emission from the light source is maintained at the minimum light amount (Min), the pulse width tw (eventually, a duty ratio) of the current drive pulse to be supplied to the light source is adjusted by PWM control (see FIG. 8B). Furthermore, in a case of manual adjustment by the operator (user) via the software keys 500 and 502 (see FIG. 6), the amount of light emitted from the light source is adjusted, for example, in the range of INDEX from "17" to "1".

In the PWM control of the light emission of the light to be sent to the rigid endoscope 18, the light emission cycle TL of the light source (the first light source 42 and/or the second light source 43) of the light source device 13 is constant regardless of the target light emission amount (that is, the value of INDEX) of the light source device 13. In other words, regardless of the pulse width tw of the current drive pulse of the PWM control, the light emission cycle TL of the light source device 13 coincides with the exposure cycle TR of each horizontal line of the imaging device 11, and the light source device 13 performs light emission of one pulse for one vertical synchronization signal in the imaging device 11 (imaging element 52).

<Light Emission Control for Ring Light>

Next, light emission control of the light source device 13 of light (for example, visible light such as white light) to be sent to the ring light 19 will be described with reference to FIGS. 10A to 10C while referring to FIG. 7. FIGS. 10A to 10C are views illustrating an aspect in which a display form transitions according to determination of the acquisition unit 64. FIGS. 10A and 10C are views illustrating an example in which the acquisition unit 64 determines that the irradiation environment information does not include an open field, and FIG. 10B is a view illustrating an example in which the acquisition unit 64 determines that the irradiation environment information includes an open field.

As described above, in a case where the light emission amount is manually adjusted by the operator (user) via the software keys 500 and 502 (see FIG. 7), the light emission amount is, for example, limited to the range of INDEX from "17" to "9". As a result, a range of light emission (INDEX from "8" to "1") in which flickering is felt by human eyes is disabled.

In FIG. 10A, the acquisition unit 64 determines that the irradiation environment information does not include an open field, and thus, INDEX "1" may be set. In this state, if connection to the light source device 13 is changed from the rigid endoscope 18 to the ring light 19, the acquisition unit 64 determines that the irradiation environment information includes an open field. As a result, the control unit 60 (see FIGS. 4 and 5) changes the software keys 500 and 502 (see FIG. 6) for rigid endoscope 18 to the software keys 500 and 502 (see FIG. 7) for ring light 19. According to this change processing, INDEX "9" is set for the software keys 500 and 502 (see FIG. 7) for ring light 19. As described above, in a case where INDEX from "1" to "8" is set for the software keys 500 and 502 (see FIG. 6) for rigid endoscope 18, INDEX "9" is set for the software keys 500 and 502 (see FIG. 7) for ring light 19. As a result, even if the INDEX of the software keys 500 and 502 (see FIG. 6) for rigid endoscope 18 is set to the range of light emission (INDEX from "8" to "1") in which flickering is felt by human eyes, INDEX "9" is set for the software keys 500 and 502 (see FIG. 7) for ring light 19, and thus, the range of light emission (INDEX from "8" to "1") in which flickering is felt by human eyes is disabled, so that there is no opportunity to make human eyes feel flickering.

Furthermore, in a case where INDEX "9" is set for the software keys 500 and 502 (see FIG. 7) for ring light 19, the control unit 60 (see FIGS. 4 and 5) can also display an error code 506 on the touch panel 65. This makes it possible to grasp that the setting range is invalid. Next, as illustrated in FIG. 10C, if connection to the light source device 13 is changed from the ring light 19 to the rigid endoscope 18, the INDEX for the software keys 500 and 502 (see FIG. 7) for ring light 19, for example, "9" is taken over by the INDEX for the software keys 500 and 502 (see FIG. 6) for rigid endoscope 18. In this manner, in a case where the light emission amount is manually adjusted by the operator (user) via the software keys 500, 502 (see FIG. 7), the light emission amount is, for example, limited to the range of INDEX from "17" to "9". As a result, a range of light emission (INDEX from "8" to "1") in which flickering is felt by human eyes is disabled.

[Adjustment of Focal Position]

In a case where the rigid endoscope 18 is connected to the imaging device 11, automatic adjustment (autofocus) of an imaging focal position may be performed by the control unit 50 of the imaging device 11, or manual adjustment (manual focus) of the imaging focal position may be performed.

On the other hand, in a case where the ring light 19 is connected to the imaging device 11, it is difficult to stably and accurately perform autofocus on the basis of the captured image. Thus, the imaging device 11 preferably performs imaging in a manual focus mode.

As described above, in the first mode, the control device 12 can control the imaging device 11 (control unit 40) such that the focal position of the imaging device 11 is adjusted by autofocus on the basis of the captured image acquired by the imaging device 11 connected to the rigid endoscope 18. However, even in such a case, the control device 12 (control unit 60) preferably controls the imaging device 11 (control unit 40) such that the focal position of the imaging device 11 connected to the ring light 19 is manually adjusted in the second mode.

In a case where the illumination light L0 is excitation light (narrow band light) for exciting a phosphor (fluorescent staining reagent), it is difficult to stably and accurately perform autofocus on the basis of contrast (contrast). Thus, in this case, the control device 12 (control unit 60) preferably controls the imaging device 11 (control unit 40) such that imaging is performed in the manual focus mode.

Determination Example 1 of Acquisition Unit

Furthermore, the acquisition unit 64 may acquire input information from the user (such as the operator) and may determine whether a device to be connected to the light source device 13 is the rigid endoscope 18 or the ring light 19. In other words, the acquisition unit 64 determines whether or not an open field is included using the input information acquired from the user (such as the operator) as the irradiation environment information.

In this case, the control device 12 includes at least an instruction acceptance unit that accepts an instruction of the illumination mode of either the first mode or the second mode. Specifically, the instruction acceptance unit accepts an instruction from the user, which indicates which illumination mode is selected from the first mode in which light is sent from the light source device 13 to the rigid endoscope 18 and the second mode in which light is sent from the light source device 13 to the ring light 19. Then, the acquisition unit 64 controls light emission of the light source device 13 on the basis of the illumination mode indicated by the instruction from the user accepted by the instruction acceptance unit.

The "instruction acceptance unit that accepts an instruction from the user" described herein can take any form. For example, the input unit 65 such as a touch panel or an input button included in the control device 12 may function as the "instruction acceptance unit" described herein. In this case, the user operates the input unit 65 to manually input information (for example, a device to be actually connected to the light source device 13) directly or indirectly indicating the illumination mode.

Alternatively, in a case where information input by the user via the operation unit (not illustrated) of the rigid endoscope 18 is transmitted to the control unit 60 via the communication unit 61 (see FIG. 4) of the control device 12, the communication unit 61 functions as the "instruction acceptance unit" of the control device 12. Alternatively, the instruction of the illumination mode of either the first mode or the second mode may be transmitted from the light source device 13 to the instruction acceptance unit of the control device 12.

For example, in a case where the light source device 13 includes an information input unit (not illustrated) that accepts information input from the user, the information input to the information input unit may include an instruction of the illumination mode of either the first mode or the second mode. In such a case, an instruction of the illumination mode of either the first mode or the second mode may be transmitted from the control unit 40 of the light source device 13 to the control unit 60 of the control device 12. In this case, the control unit 60 substantially functions as the instruction acceptance unit.

Second Determination Example of Acquisition Unit

The acquisition unit 64 of the control device 12 may determine the illumination mode on the basis of a type of the light guide unit (light guide) connected to the light source device 13. The acquisition unit 64 is connected to the connector 45 and acquires information indicating the type of the light guide connected to the connector 45 from the connector 45. The type of the light guide connected to the connector 45 is determined on the basis of a device connected to the light source device 13 (the rigid endoscope 18 (see FIG. 4)/the ring light 19 (see FIG. 5)) and indicates the device connected to the light source device 13. In other words, the acquisition unit 64 determines whether or not an open field is included using the type of the light guide unit (light guide) connected to the connector 45 of the light source device 13 as the irradiation environment information.

In this case, the rigid endoscope 18 is connected to the light source device 13 via a first-type light guide unit (light guide 16; see FIGS. 1, 2, and 4), and the ring light 19 is connected to the light source device 13 via a second-type light guide unit (light guide 32; see FIGS. 3 and 5).

Thus, which illumination mode is selected between the first mode in which light is sent from the light source device 13 to the rigid endoscope 18 and the second mode in which light is sent from the light source device 13 to the ring light 19 is determined on the basis of the type of the light guide unit connected to the light source device 13. Thus, the control device 12 controls light emission of the light source device 13 on the basis of the type of the light guide unit connected to the light source device 13.

Note that a method by which the control device 12 determines the type of the light guide unit connected to the light source device 13 is not limited. For example, a shape of a connection terminal of the light source device 13 with respect to the connector 45 and a connection point in the connector 45 may be different between the first-type light guide unit (the light guide 16 (see FIG. 4)) and the second-type light guide unit (the light guide 32 (see FIG. 5)). Information indicating the type of the light guide unit connected to the connector 45 may be transmitted from the connector 45 to the control unit 40 of the light source device 13, and then transmitted from the control unit 40 to the control unit 60 of the control device 12.

Determination Example 3 of Acquisition Unit

The acquisition unit 64 of the control device 12 may determine the illumination mode on the basis of the captured image output from the imaging device 11 that captures the light from the four subjects 90 (subjects). As an example, the control device 12 (acquisition unit 64) may determine whether the device connected to the light source device 13 is the rigid endoscope 18 or the ring light 19 on the basis of a mask region in the captured image.

In this case, the rigid endoscope 18 in a state of being attached to the imaging device 11 causes the imaging device 11 to receive the observation light L1 while shielding part of the observation light L1 (imaging light) from the subject 90 in a form different from the ring light 19 in a state of being attached to the imaging device 11. The control unit 60 of control device 12 determines the illumination mode on the basis of the light shielding portion in the captured image output from imaging device 11. As described above, which illumination mode is selected between the first mode in which light is sent from the light source device 13 to the rigid endoscope 18 and the second mode in which light is sent from the light source device 13 to the ring light 19 is determined on the basis of the light shielding portion in the captured image output from the imaging device 11. Thus, the control device 12 controls light emission of the light source device 13 on the basis of the light shielding portion in the captured image.

Figure 11:
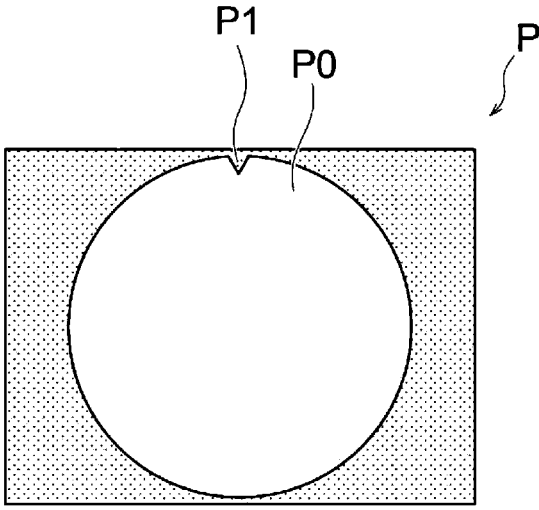
FIG. 11 is a view illustrating an example of a captured image acquired by an imaging device via the rigid endoscope.
Figure 12:
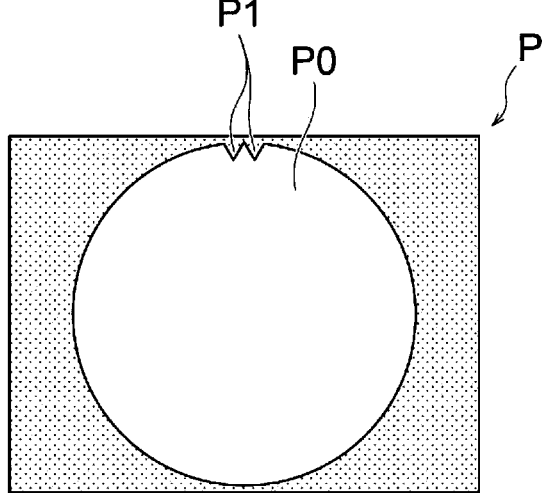
FIG. 12 is a view illustrating an example of a captured image acquired by an imaging device via the ring light.

FIG. 11 is a view illustrating an example of a captured image P (particularly, a light shielding portion P1) acquired by the imaging device 11 via the rigid endoscope 18. FIG. 12 is a view illustrating an example of the captured image P (particularly, the light shielding portion P1) acquired by the imaging device 11 via the ring light 19.

As illustrated in FIGS. 11 and 12, the captured image P includes an observation image P0 and the light shielding portion P1. The observation image P0 corresponds to a substantial light receiving portion of the observation light L1 in the imaging element 52 of the imaging device 11 and is an image representing the observation target. The light shielding portion P1 corresponds to a portion of the observation light L1 that is shielded by the rigid endoscope 18 or the ring light 19 and corresponds to a portion of the imaging element 52 that does not substantially receive the observation light L1.

Each of the rigid endoscope 18 (for example, the imaging connection portion 23) and the ring light 19 (for example, the imaging connection portion 33) has a light shielding portion having a specific shape and can provide the light shielding portion P1 having the specific shape to the captured image P (see FIGS. 10A to 11). The control device 12 (for example, the normal light processing unit 62a or the special light processing unit 62b of the image generation unit 62) analyzes the captured image P and extracts features such as the shape of the light shielding portion P1. Then, the control device 12 can determine a device connected to the light source device 13 on the basis of the extracted features of the light shielding portion P1 and can control light emission of the light source device 13 on the basis of the determination result. In other words, the acquisition unit 64 determines whether or not an open field is included using the features of the light shielding portion P1 as the irradiation environment information.

Determination Example 4 of Acquisition Unit

Furthermore, the acquisition unit 64 may determine whether the captured image is an endoscopic image or an operative field image and may determine whether the device connected to the light source device 13 is the rigid endoscope 18 or the ring light 19. In other words, the acquisition unit 64 has a recognition function of recognizing a category of the captured image and determines whether or not an open field is included on the basis of the category. This category is an endoscopic image or an operative field image. Furthermore, the recognition function may be implemented by artificial intelligence (AI), or the like. In this manner, the acquisition unit 64 can determine whether the image is an endoscopic image or an operative field image using AI, or the like, capable of recognizing an object. Alternatively, the acquisition unit 64 may determine whether the captured image is an endoscopic image or an operative field image, for example, by analyzing frequency distribution of the captured image.

Determination Example 5 of Acquisition Unit

Furthermore, the acquisition unit 64 determines whether or not an open field is included in the captured image, for example, by a detection signal from the trocar. In other words, the acquisition unit 64 determines whether or not an open field is included using the detection signal from the trocar as the irradiation environment information. More specifically, in a case where a signal indicating that the endoscope has been inserted from the trocar is acquired, the acquisition unit 64 determines that an open field is not included.

Figure 13:
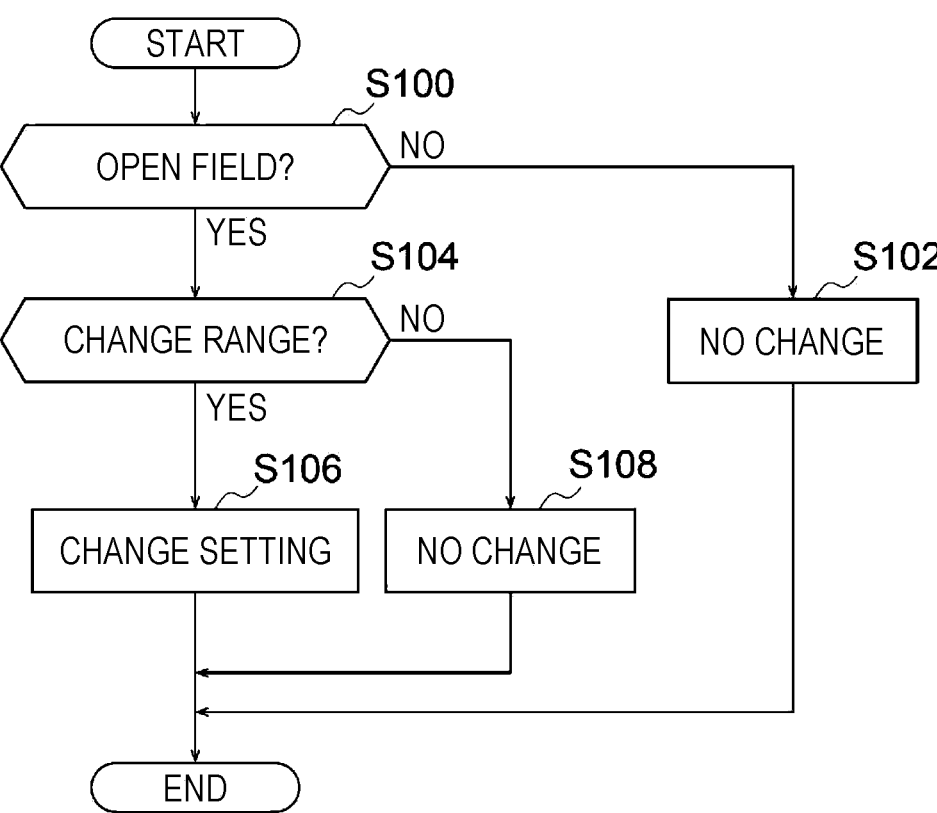
FIG. 13 is a flowchart indicating an example of processing of reducing blinking light emission.

FIG. 13 is a flowchart indicating an example of processing of reducing blinking light emission. As illustrated in FIG. 13, the acquisition unit 64 acquires the irradiation environment information and determines whether or not an open field is included (step S100). In a case where the acquisition unit 64 determines that an open field is not included (step S100: N), the control unit 60 maintains a state in which the INDEX of the software keys 500 and 502 (see FIG. 6) for rigid endoscope 18 is not changed (step S102) and ends the processing.

On the other hand, in a case where the acquisition unit 64 determines that an open field is included (step S100: Y), the control unit 60 further determines whether or not the INDEX of the software keys 500 and 502 (see FIG. 7) is in a change range (step S104). In a case where the control unit 60 determines that INDEX is in the change range (step S104: Y), the control unit 60 changes the setting of INDEX (step S106) and ends the processing. On the other hand, in a case where it is determined that the INDEX is not in the change range (step S104: N), the control unit 60 maintains the setting of the INDEX (step S106) and ends the processing.

Figure 14:
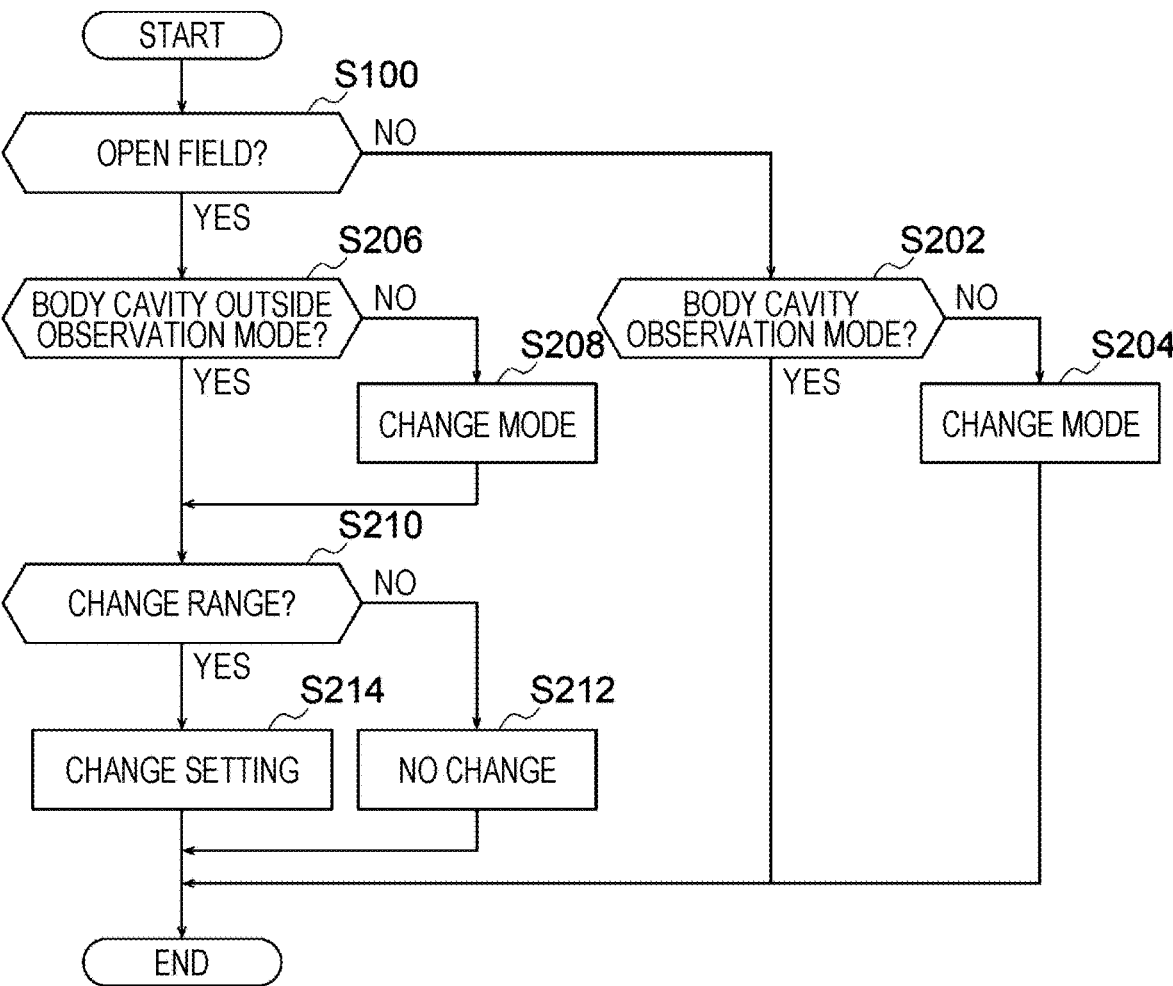
FIG. 14 is a flowchart indicating an example of processing including mode change.

FIG. 14 is a flowchart indicating a processing example including mode change. As indicated in FIG. 14, the acquisition unit 64 acquires the irradiation environment information and determines whether or not an open field is included (step S100). In a case where the acquisition unit 64 determines that an open field is not included (step S100: N), the control unit 60 determines whether or not the mode is the body cavity observation mode (step S202). In a case where it is determined that the mode is not the body cavity observation mode (step S202: N), the control unit 60 changes the mode to the body cavity observation mode. In other words, setting is changed to setting for the software keys 500 and 502 (see FIG. 6) for rigid endoscope 18. On the other hand, in a case where it is determined that the mode is the body cavity observation mode (step S202: Y), the control unit 60 maintains the body cavity observation mode and ends the processing.

On the other hand, in a case where the acquisition unit 64 determines that an open field is included (S100: Y), the control unit 60 determines whether or not the mode is the body cavity outside observation mode (step S206). In a case where it is determined that the mode is not the body cavity outside observation mode (step S206: N), the control unit 60 changes the mode to the body cavity outside observation mode. In other words, setting is changed to setting for the software keys 500 and 502 (see FIG. 7) for ring light 19. On the other hand, in a case where it is determined that the mode is the body cavity outside observation mode (step S206: Y), the control unit 60 maintains the body cavity inside observation mode. Next, the control unit 60 further determines whether or not the INDEX of the software keys 500 and 502 (see FIG. 7) is in the change range (step S210). In a case where the control unit 60 determines that INDEX is in the change range (step S210: Y), the control unit 60 changes the setting of INDEX (step S214) and ends the processing. On the other hand, in a case where it is determined that the INDEX is not in the change range (step S210: N), the control unit 60 60 maintains the setting of the INDEX (step S212) and ends the processing.

As described above, according to the present embodiment, the acquisition unit 64 acquires the irradiation environment information regarding the irradiation environment of the irradiation light, and the control unit 60 displays the software keys 500 and 502 for ring light 19 on the touch panel 65 in a case where the irradiation environment information acquired by the acquisition unit 64 includes an open field, and displays the software keys 500 and 502 for rigid endoscope 18 on the touch panel 65 in a case where the irradiation environment information does not include an open field.

In the software keys 500 and 502 for ring light 19, the function corresponding to light emission that causes flickering that can be sensed by human eyes is disabled, and in the software keys 500 and 502 for rigid endoscope 18, the function corresponding to light emission that causes flickering that can be sensed by human eyes is enabled. As a result, in the irradiation light emitted by the ring light 19, light emission that causes flickering that can be sensed by human eyes is disabled, and flickering can be prevented from occurring in a situation where light enters the eyes of the operator, or the like. On the other hand, the irradiation light emitted by the rigid endoscope 18 can be emitted at a target frequency.

First Modification of First Embodiment

The observation system 10 according to the first modification of the first embodiment is different from the observation system 10 according to the first embodiment in that the target values of brightness associated with the INDEX are different between the software keys 500 and 502 (see FIG. 6) for rigid endoscope 18 and the software keys 500 and 502 (see FIG. 7) for ring light 19. Hereinafter, differences from the observation system 10 according to the first embodiment will be described.

FIG. 15 is a table indicating target values of brightness associated with INDEX of the software keys 500 and 502 (see FIG. 7) for ring light 19. As indicated in FIG. 15, INDEX [9] is associated with INDEX [1] to [8]. As a result, even if the setting is changed to INDEX from [1] to [8] for display for the software keys 500 and 502 (see FIG. 6), INDEX [9] is set. As a result, INDEX from [1] to [8] that causes human eyes to feel flickering are disabled.

Figures 16A, 16B:
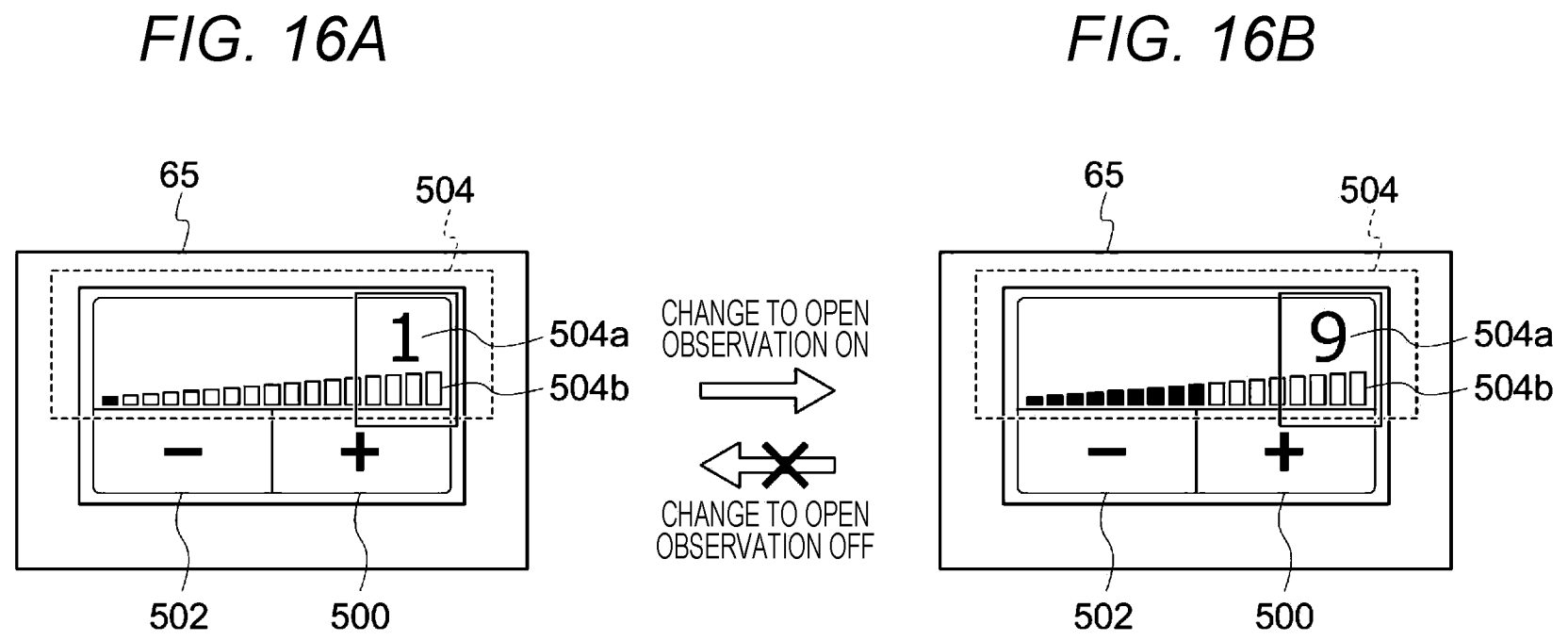

FIGS. 16A and 16B are views illustrating an aspect in which the determination of the acquisition unit 64 transitions. FIG. 16A is a view illustrating an example in which the acquisition unit 64 determines that the irradiation environment information does not include an open field, and FIG. 16B is a view illustrating an example in which the acquisition unit 64 determines that the irradiation environment information includes an open field.

In FIG. 16A, the acquisition unit 64 determines that the irradiation environment information does not include an open field, and thus, the INDEX "1" for display is displayed in the region 504 as the numerical value 504*a*, and "1" is also set for the INDEX for setting.

In FIG. 16B, the acquisition unit 64 determines that the irradiation environment information includes an open field, and thus, INDEX "9" for display is displayed in the region 504 as the numerical value 504*a*, and "9" (see FIG. 15) is set in the INDEX for setting.

As described above, in the software keys 500 and 502 (see FIG. 6) according to the present embodiment, INDEX [9] is set even if the setting is changed to INDEX from [1] to [8] for display. As a result, INDEX from [1] to [8] that causes human eyes to feel flickering are disabled.

Second Embodiment

The observation system 10 according to a second embodiment is different from the observation system 10 according to the first embodiment in that even in a case where the ring light 19 is connected to the light source device 13, pulsed light that does not cause human eyes to feel flickering is emitted. Hereinafter, differences from the observation system 10 according to the first embodiment will be described. [Second Light Emission Adjustment Example Regarding Ring Light]

Figures 17A, 17B:
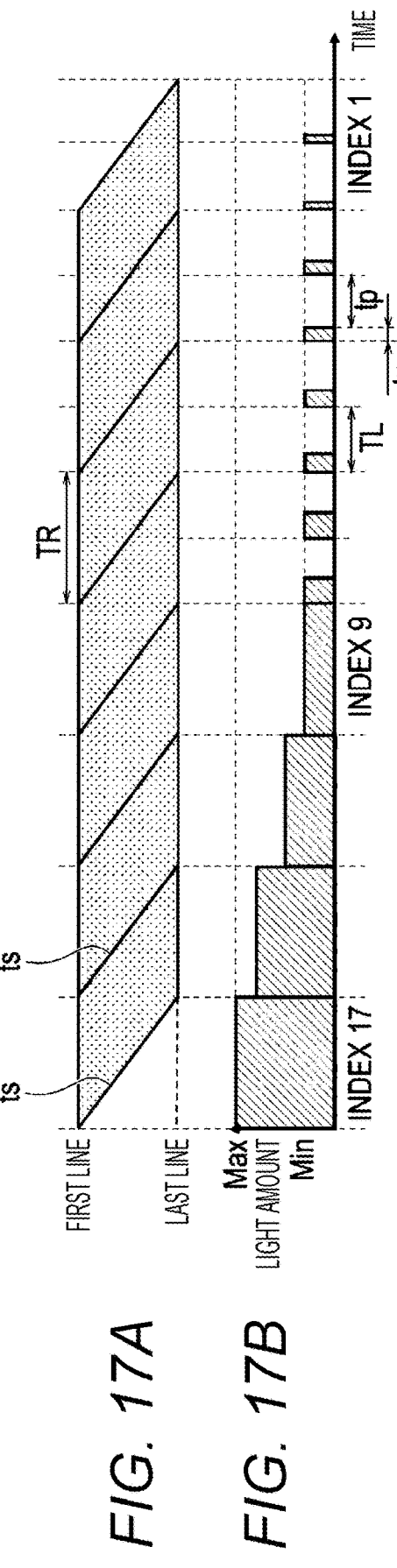
FIGS. 17A and 17B are views illustrating a second light emission adjustment example from a case where the target light amount is maximum to a case where the target light amount is minimum.

FIGS. 17A to 18B are views for explaining a second light emission adjustment example. FIGS. 17A to 18B are views illustrating a case where light (for example, white light) is supplied from the light source device 13 to the ring light 19. FIGS. 17A and 17B are views illustrating a second light emission adjustment example from a case where the target light amount of light emission of the light source device 13 is maximum (INDEX 17) to a case where the target light amount is minimum (INDEX 1).

Figures 18A, 18B:
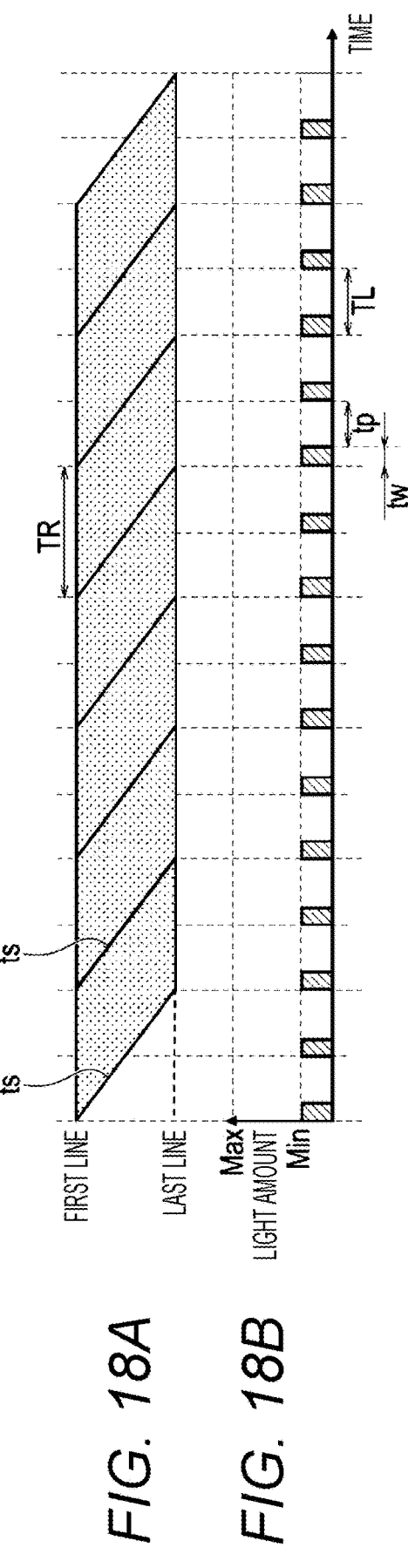
FIGS. 18A and 18B are views for explaining PWM control according to the second light emission adjustment example.

FIGS. 18A and 18B are views illustrating PWM control (INDEX 5) of the second light emission adjustment example.

FIGS. 17A and 18A indicate an exposure state of the imaging element 52 (see FIGS. 4 and 5), indicates a horizontal line of the imaging element 52 on a vertical axis, and indicates time on a horizontal axis. In FIGS. 17A and 18A, an uppermost line indicates an uppermost horizontal line (that is, a first line), and a lowermost line indicates a lowermost horizontal line (that is, a last line). A line (oblique line) indicated by a reference sign "ts" indicates a pixel data reading start timing of each horizontal line regarding each captured image.

FIGS. 17B and 18B indicate light emission timings and light amounts of the light source (the first light source 42 and/or the second light source 43 (see FIGS. 4 and 5)). FIGS. 17B and 18B indicate the light emission amount of the light source (that is, intensity of the illumination light L0 sent from the light source device 13 to the rigid endoscope 18 or the ring light 19) on a vertical axis. FIGS. 17B and 18B indicate time on a horizontal axis, indicates a continuous light emission period (that is, a light emission period of one pulse), and eventually indicates an applied pulse (current drive pulse) of a current to be supplied to the light source. Note that a value m of "INDEX" (where "m" is an integer from 1 to 17) represents a degree of a target light amount of light emission of the light source device 13, and as "m" is greater (closer to "17"), the target light amount becomes larger, and as "m" is smaller (closer to "1"), the target light amount becomes smaller. Furthermore, "TR" indicates an exposure cycle of each horizontal line of the imaging element 52, and "TL" indicates a light emission cycle of the light source device 13. Furthermore, "tw" indicates a pulse width of light emission of the light source device 13 (that is, a pulse width of a current drive pulse to be supplied to the light source device 13). Furthermore, "tp" indicates an interval between adjacent light emission pulses of the light source device 13 (that is, a time interval between adjacent drive pulses of the current to be supplied to the light source device 13).

While the target light emission amount of the light source device 13 is relatively large (for example, in a case of INDEX from "17" to "9"), the current value to be supplied to the light source is adjusted and the light emission amount itself from the light source is adjusted in a similar manner to the light emission control related to the rigid endoscope 18 described above (see FIG. 17B). On the other hand, in a case where the target light emission amount of the light source device 13 is relatively small (for example, in a case of INDEX from "8" to "1"), the light emission cycle (the cycle in which the drive pulse is ON) is adjusted in addition to the pulse modulation control (PWM control) of the current drive pulse to be supplied to the light source.

In other words, light emission (drive pulse-ON) and non-light emission (drive pulse-OFF) are periodically repeated in the light emission control (pulse modulation control) regarding the ring light 19 in a similar manner to the PWM control related to the rigid endoscope 18 described above. However, in the light emission control (pulse modulation control) regarding the ring light 19, the light emission cycle TL is set to ½ and the light emission frequency is set to double compared with the PWM control related to the rigid endoscope 18 described above. In other words, the light emission cycle TL of the light source device 13 coincides with ½ of the exposure cycle TR of each horizontal line of the imaging device 11, and the light source device 13 emits light twice with respect to one vertical synchronization signal in the imaging device 11 (imaging element 52).

Furthermore, in a state where the amount of light emitted from the light source is maintained at the minimum light amount (Min), the pulse width tw of the current drive pulse to be supplied to the light source is set to ½ of the pulse width tw in the PWM control related to the rigid endoscope 18. Thus, the duty ratio (=pulse width tw/light emission cycle TL) in the light emission control related to the ring light 19 is the same as the duty ratio in the light emission control related to the rigid endoscope 18 described above.

For example, in a case where the light emission frequency of the pulse modulation control related to the rigid endoscope 18 is 50 Hz, the light emission frequency of the pulse modulation control related to the ring light 19 may be set to 100 Hz. Similarly, in a case where the light emission frequency of the pulse modulation control related to the rigid endoscope 18 is 60 Hz, the light emission frequency of the pulse modulation control related to the ring light 19 may be set to 120 Hz.

In the examples illustrated in FIGS. 8A to 9B, a ratio of the light emission frequency of the pulse modulation control of the ring light 19 to the light emission frequency of the pulse modulation control of the rigid endoscope 18 is set to "2", but may be "4", for example.

In this case, in a case where the light emission frequency of the pulse modulation control related to the rigid endoscope 18 is 50 Hz or 60 Hz, the light emission frequency of the pulse modulation control related to the ring light 19 is set to 200 Hz or 240 Hz.

Figures 19, 20:
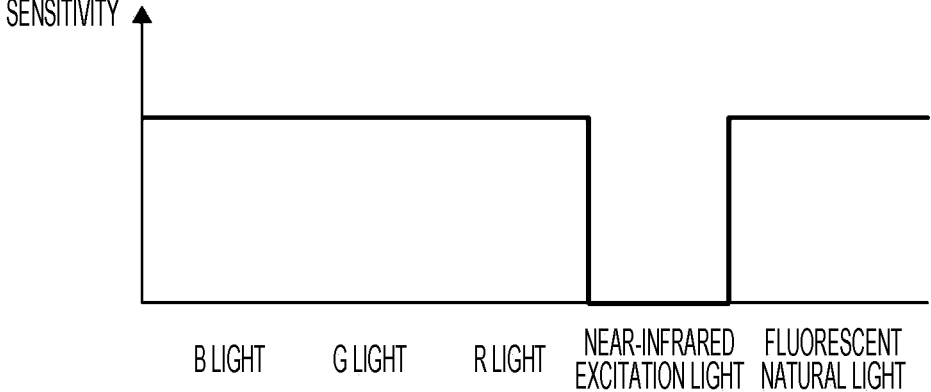
FIG. 19 is a table indicating target values of brightness associated with software keys for ring light.
FIG. 20 is a view for explaining sensitivity of an imaging element according to the present embodiment.

FIG. 19 is a table indicating target values of brightness associated with INDEX of the software keys 500 and 502 (see FIG. 7) for ring light 19 in the second light emission adjustment example. As indicated in FIG. 19, INDEX from [1] to [17] for display are associated with INDEX from [1] to [17] for setting. As a result, if the setting is changed to INDEX from [1] to [17] for display for the software keys 500 and 502 (see FIG. 7), INDEX from [1] to [17] for setting is set. In other words, a range of frequencies associated with INDEX from [8] to [1] of the software keys 500 and 502 (see FIG. 7) for ring light 19 is made different from a range of frequencies associated with INDEX from [8] to [1] of the software keys 500 and 502 (see FIG. 7) for rigid endoscope 18.

The frequency of blinking that can be recognized by a human is generally said to be 50 to 60 Hz (however, it varies depending on individual differences and fatigue states, and for example, when tired, blinking may not be recognized even at about 30 Hz). As a result, even if INDEX from [1] to [8] for setting is set, the light emission frequency of the pulse modulation control is set to 100 Hz, and thus, a situation where the human eyes feel flickering is prevented. Note that white light having intensity lower than that in a tw period may be emitted during a tp period. In this case, a luminosity difference between the tp period and the tw period decreases, and flickering is reduced.

Furthermore, as standards for video content, ISO 9241-391 specifies to avoid flashes 3 times or more per second and less than 65 times. In the present embodiment, the light emission frequency of the pulse modulation control for the ring light 19 is set to equal to or higher than 100 Hz, and thus, blinking is not recognized and flickering is not felt. Note that in the present embodiment, the light emission frequency of the pulse modulation control has been described as 100 Hz or 120 Hz, but the present disclosure is not limited thereto. For example, the light emission frequency of the pulse modulation control may be a frequency equal to or higher than 65 Hz. If the light emission frequency of the pulse modulation control is equal to or higher than 65 Hz, blinking is not recognized, so that there is no problem of botheration.

On the other hand, even if the light emission frequency of the pulse modulation control is less than a predetermined value, botheration of blinking is allowed. For example, in a case where the light emission frequency of the pulse modulation control is blinking at a frequency of less than 3 Hz, blinking is recognized, but botheration is allowed. In addition, 0 Hz, that is, a state of not blinking does not cause a problem of botheration.

As illustrated in FIG. 18B, in a case where the first state (tp period) and the second state (tw period) in which light emission intensity in a band of visible light is higher than that in the first state are periodically repeated, a length of the tw period in the second state also causes people to feel flickering.

For example, a period of one cycle at a frequency of 65 Hz is about 15.4 ms, and the half cycle is about 7.7 ms. In a visual psychological experiment, if the tw period of the second state is equal to or shorter than 7.7 ms, the state is not recognized, and thus, there is no problem of botheration. Furthermore, one cycle of 60 Hz is about 16.7 ms, and blinking is switched every about 8.3 ms at a duty ratio of 50%, and flickering is recognized. On the other hand, if one cycle of 60 Hz is about 16.7 ms and the duty ratio is 40%:60%, the tw period of the second state and the first state (tp period) become 6.7 ms:10 ms, and the period of 6.7 ms is in an unrecognized region, so that flickering is not felt by human eyes even at 60 Hz.

As described above, according to the present embodiment, in a case of using pulse modulation control using pulsed light for the ring light 19, a range associated with the target value of frequency even in the same range of INDEX from [8] to [1] as that for the rigid endoscope 18 is set as a range that does not cause flickering that can be sensed by human eyes. This makes it possible to prevent flickering from occurring even in a situation where the irradiation light emitted from the ring light 19 comes into the eyes of the operator, or the like.

Third Embodiment

The observation system 10 according to a third embodiment is different from the observation system 10 according to the first embodiment in that fluorescence imaging light can be further emitted. Hereinafter, differences from the observation system 10 according to the first embodiment will be described.

FIG. 20 is a view for explaining sensitivity of the imaging element 52 (see FIGS. 4 and 5) according to the present embodiment. For example, an observation filter is provided on an optical path L1. The white light according to the present embodiment mainly includes light in a blue wavelength band (B light), light in a green wavelength band (G light), and light in a red wavelength band (R light). On the other hand, the excitation light is light in a near-infrared wavelength band. In FIG. 20, light has a larger wavelength toward the right side. A wavelength band of the light to be used as the near-infrared excitation light is, for example, 700 nm to 800 nm. Hereinafter, it is referred to as excitation light. A wavelength of the fluorescence is larger than a wavelength of the near-infrared light that is used and includes fluorescence due to indocyanine green and fluorescence derived from a light source.

Figures 21A, 21B:
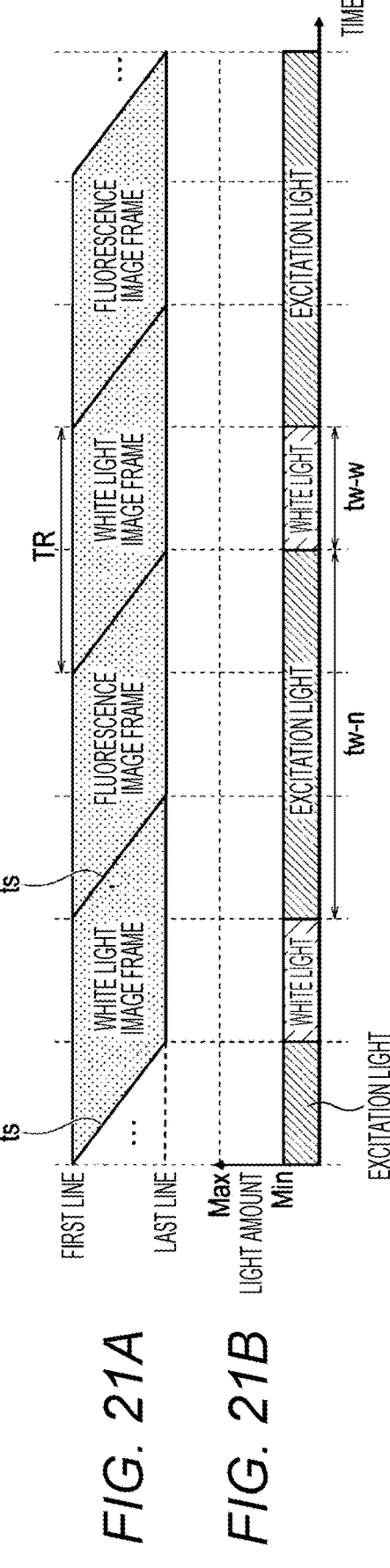
FIGS. 21A and 21B are views illustrating an example of a captured image acquired by the imaging device via the rigid endoscope.
Figures 22A, 22B:
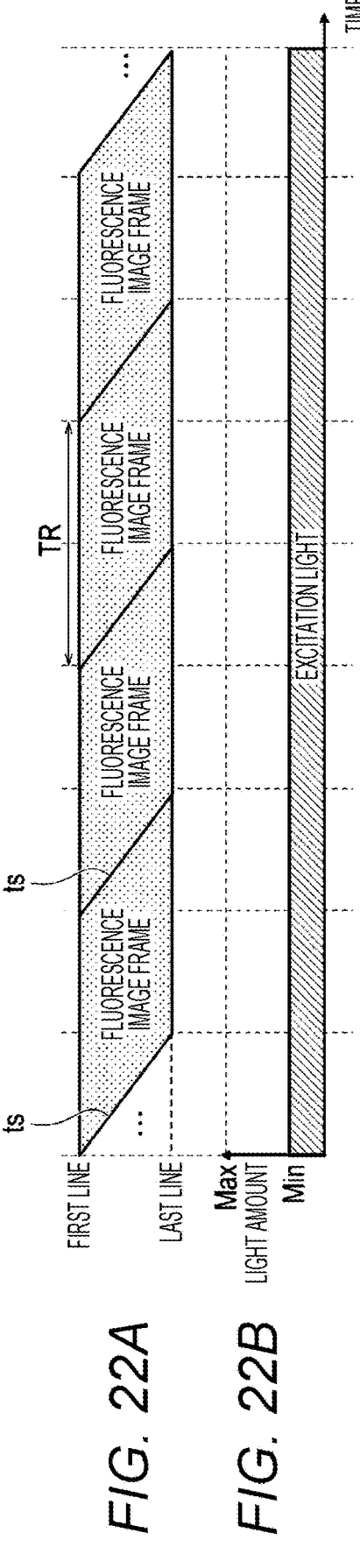
FIGS. 22A and 22B are views illustrating a case where light is supplied to the ring light.

FIGS. 21A and 21B are views illustrating a case where light (particularly, white light and excitation light (narrow band light)) is supplied from the light source device 13 to the rigid endoscope 18, and FIGS. 22A and 22B are views illustrating a case where light (excitation light (narrow band light (for example, visible light)) is supplied from the light source device 13 to the ring light 19. FIGS. 21A to 22B illustrate reference states of light emission control of the light source device 13. By reducing a pulse width, a light amount can be reduced from the reference state.

In FIG. 21A, a "fluorescence image frame" indicates a range in which one fluorescence image is acquired as a captured image, and a "white light image frame" indicates a range in which one reflected light image of white light is acquired as a captured image. In FIG. 21B, "excitation light" indicates a pulse of excitation light, and "white light" indicates a pulse of white light.

<Light Emission Control for Rigid Endoscope>

First, an example of light emission control of light sent from the light source device 13 to the rigid endoscope 18 will be described with reference to FIGS. 21A and 21B.

In the present example, the white light and the excitation light emitted in a time-division manner by the light source device 13 are sent to the rigid endoscope 18. In other words, the control device 12 controls light emission of the light source device 13 so that the light source device 13 emits white light and excitation light (narrow band light) in a time-division manner in the first mode in which light is sent from the light source device 13 to the rigid endoscope 18.

By causing the light source device 13 to emit the white light and the excitation light separately in terms of time, both the reflected light image of the white light and the fluorescence image of the excitation light can be generated and acquired by the single imaging element 52. Then, the control device 12 controls the light source device 13 by PWM control to adjust light emission amounts of the white light and the excitation light in the light source device 13. In other words, a pulse width (tw-w, tw-n) of the current drive pulse to be supplied to each of the white light source (the first light source 42 (see FIG. 4)) and the excitation light source (the second light source 43 (see FIG. 4)) is adjusted, and the light emission amounts of the white light and the excitation light in the light source device 13 are adjusted. Note that a minimum pulse width (tw-w, tw-n) can be set to an arbitrary value (for example, 166 μs (microsecond)).

Also in this case, as illustrated in FIG. 21B, the first state (tw-w period) and the second state (tw-n period) in which the light emission intensity in the band of visible light is higher than that in the first state are periodically repeated. As a result, in a case where such pulsed light is erroneously sent to the ring light 19, a length of the tw period in the second state also causes human eyes to feel flickering.

As described above, switching between the first state and the second state includes a case where the emission state of the white light and emission of the excitation light for fluorescence observation are switched. Furthermore, switching between the first state and the second state may include switching between the emission state of the excitation light for fluorescence observation and the emission state of the excitation light for fluorescence observation in a wavelength band different from the emission state of the excitation light for fluorescence observation. In a case where the state is further switched, there may be a case where the light emission state of one wavelength band and the light emission state of another wavelength band are exclusively switched, or there may be a case where the light emission state of one wavelength band is continued and then the light emission state of another wavelength band is switched.

As described above, the control unit 60 of the control device 12 controls light emission of the light source device 13 so that the light source device 13 emits white light and narrow band light in a time-division manner in the first mode in which light is sent from the light source device 13 to the rigid endoscope 18. Furthermore, the control unit 60 controls the light emission amount of the light source device 13 on the basis of a pulse width modulation method.

Note that, in a similar manner to the first light emission adjustment example described above, the control device 12 may adjust the light emission amount by adjusting a current value to be supplied to the light source while the target light emission amount is relatively large. Then, after the current value to be supplied to the light source reaches the minimum light amount (Min), the control device 12 may perform PWM control while maintaining the light emission amount from the light source at the minimum light amount (Min) to adjust the pulse width (tw-w, tw-n) of the current drive pulse to be supplied to the light source.

<Light Emission Control for Ring Light>

Next, light emission control of the light source device 13 regarding light (in particular, excitation light) sent to the ring light 19 will be described with reference to FIGS. 22A and 22B.

In the present example, the excitation light (narrow band light) continuously (continuously) emitted in the light source device 13; continuous light) is sent to the ring light 19. In other words, the control device 12 controls light emission of the light source device 13 so that the light source device 13 continuously emits the excitation light (narrow band light) in the second mode in which light is sent from the light source device 13 to the ring light 19. Note that, in the present embodiment, selection between a case where white light and narrow band light are caused to be emitted in a time-division manner and a case where the excitation light (narrow band light) is caused to be continuously emitted may be referred to as selection of a fluorescence wavelength or an excitation wavelength.

Then, the control device 12 controls a timing of an electronic shutter in the imaging element 52 of the imaging device 11 to adjust a substantial light reception amount in the imaging element 52.

In the example illustrated in FIGS. 22A and 22B, the timing of the electronic shutter is controlled by adjusting the pixel data reading start timing (exposure start timing) ts of the horizontal line of the imaging element 52 of the imaging device 11. In other words, in each exposure cycle TR, by delaying the pixel data reading start timing ts from the reference state, a substantial exposure amount (fluorescent image frame) in the imaging element 52 is reduced. By controlling the timing of the electronic shutter in the imaging element 52 in this manner and adjusting the substantial exposure period, an amount of the observation light L1 received in the imaging element 52 can be adjusted. Note that the timing of the electronic shutter may be controlled by adjusting a pixel data reading end timing (exposure end timing) of the horizontal line of the imaging element 52. In this manner, the control device 12 can adjust the amount of light received in the imaging element 52 as follows in the second mode in which light is sent from the light source device 13 to the ring light 19.

Figures 23A, 23B:
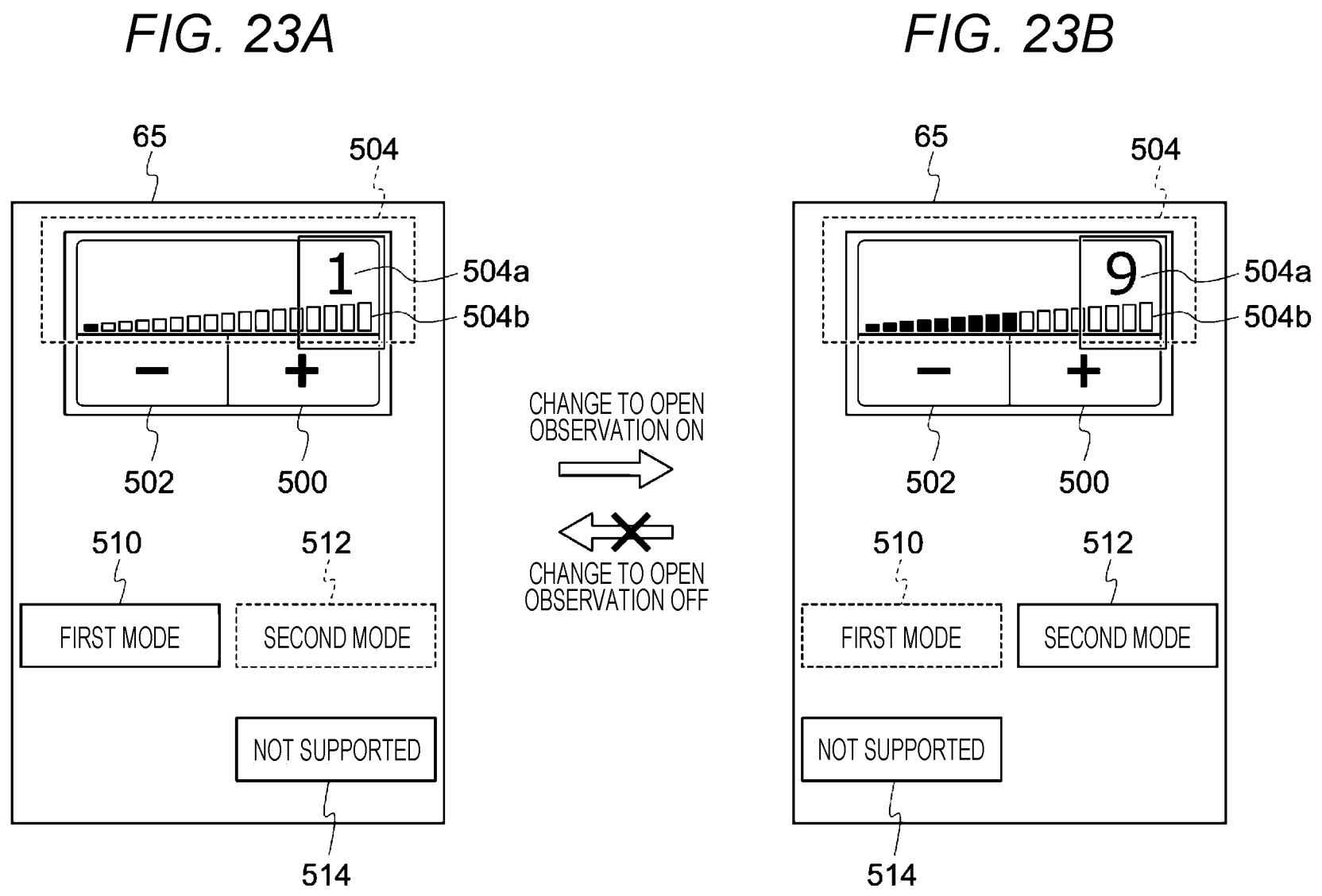

FIGS. 23A and 23B are views illustrating an aspect in which the determination of the acquisition unit 64 transitions according to fluorescence imaging. FIG. 23A is a view illustrating an example in which the acquisition unit 64 determines that the irradiation environment information does not include an open field, and FIG. 23B is a view illustrating an example in which the acquisition unit 64 determines that the irradiation environment information includes an open field. The software key 510 and the software key 512 are associated with an observation mode selection function. In other words, the software key 510 selects the first mode, and the software key 512 selects the second mode. As described above, the software key 510 and the software key 512 are a function for selecting a fluorescence wavelength or an excitation wavelength. More specifically, the software key 510 selects irradiation control for causing the white light and the narrow band light to be emitted in a time-division manner as illustrated in FIGS. 21A and 21B, and the software key 512 selects irradiation control for causing the excitation light (narrow band light) to be continuously emitted as illustrated in FIGS. 22A and 22B.

As described above, in the software key 512, the function corresponding to visible light emission is disabled, and in the software key 510, the function corresponding to visible light emission is enabled. Note that the software key 510 according to the present embodiment corresponds to a first software key, and the software key 512 corresponds to a second software key.

In FIG. 23A, the acquisition unit 64 determines that the irradiation environment information does not include an open field, and thus, the control unit 60 displays the software key 510 for selecting the first mode and grays out the software key 512 for selecting the second mode so that the software key is not selectable. If the software key 510 is instructed, the fluorescence emission related to the rigid endoscope is controlled. In this case, not only the software key 512 is unable to be depressed, but also a color, or the like, may be changed as display on the touch panel 65. For example, the software key 510 may be blue, and the software key 512 may be red. Alternatively, the software key 512 may be hidden. As described above, by changing the display form, it can be seen that the software key 512 that is disabled is inoperable or unsettable. Alternatively, it can be seen that the function is not available because the function is not displayed.

In FIG. 23A, the acquisition unit 64 determines that the irradiation environment information includes an open field, and thus, the control unit 60 displays the software key 512 for selecting the second mode and grays out the software key 512 for selecting the first mode so that the software key is not selectable. If the software key 512 is instructed, the fluorescence emission of the ring light 19 is controlled. In this case, not only the software key 510 is unable to be depressed, but also a color, or the like, may be changed as display. For example, the software key 512 may be blue, and the software key 510 may be red. Alternatively, the software key 510 may be hidden. As described above, by changing the display form, it can be seen that the software key 510 that is disabled is inoperable or unsettable. Alternatively, it can be seen that the function is not available because the function is not displayed.

As described above, in the present embodiment, in a case where the acquisition unit 64 determines that an open field is included, the software key 512 for selecting the first mode is grayed out and is made unselectable. As a result, the ring light 19 is prevented from emitting the white light and the narrow band light in a time-division manner, and light emission of the irradiation light emitted by the ring light 19 which causes flickering that can be sensed by human eyes is disabled, and in a situation where the light enters the eyes of the operator, or the like, flickering can be prevented from occurring.

Fourth Embodiment

The observation system 10 according to a fourth embodiment is different from the observation system 10 according to the first embodiment in including a first imaging element 52a and a second imaging element 52b. Hereinafter, differences from the observation system 10 according to the first embodiment will be described.

Figure 24:
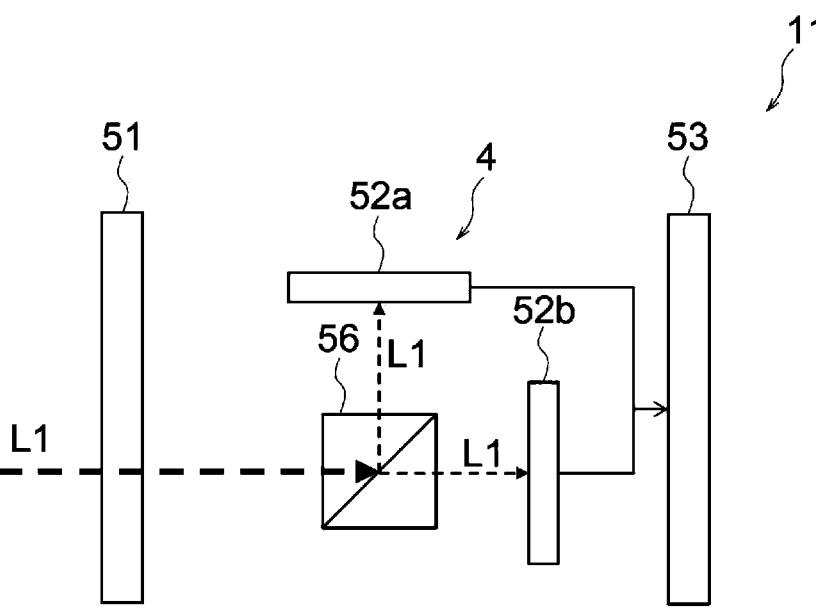
FIG. 24 is a block diagram illustrating an example of a configuration of an imaging element of the imaging device.

FIG. 24 is a block diagram illustrating an example of an imaging element configuration of the imaging device 11. The imaging device 11 includes 4 (the first imaging element 52a and the second imaging element 52b) illustrated in FIG. 24, and a wavelength separation optical element 56 that emits the observation light L1 toward the first imaging element 52a and the second imaging element 52b. The wavelength separation optical element 56 includes an arbitrary optical element such as a dichroic mirror and emits light in a specific wavelength region of the observation light L1 toward the first imaging element 52a and emits light in other wavelength regions toward the second imaging element 52b. For example, a narrow band light component (for example, a fluorescence component) in the observation light L1 may be reflected by the wavelength separation optical element 56 and received by the first imaging element 52a, and a white light component in another wavelength region may be transmitted through the wavelength separation optical element 56 and received by the second imaging element 52b. In this case, even if both the white light and the narrow band light are simultaneously emitted in the light source device 13 and simultaneously radiated on the observation target, the imaging device 11 can simultaneously and separately receive the white light and the narrow band light and separately output a captured image related to the white light and a captured image related to the narrow band light.

As described above, the imaging device 11 can employ various imaging methods. Thus, the control device 12 may change light emission control of the light source device 13 on the basis of the imaging method of the imaging device 11 that is actually connected.

Figures 25A, 25B:
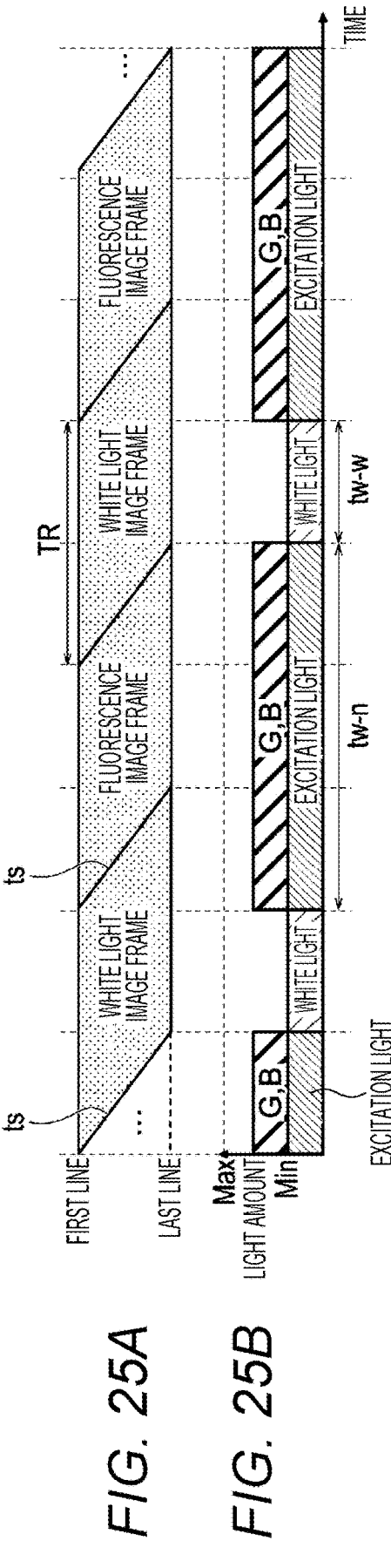
FIGS. 25A and 25B are views illustrating a case where light is supplied to the rigid endoscope.

FIGS. 25A and 25B are views illustrating a case where light (particularly, the white light and the excitation light (narrow band light)) is supplied from the light source device 13 to the rigid endoscope 18. In FIG. 25A, a "fluorescence image frame" indicates a range in which one fluorescence image is acquired as a captured image, and a "white light image frame" indicates a range in which one reflected light image of the white light is acquired as a captured image. In FIG. 25B, "excitation light" indicates a pulse of the excitation light, and "white light" indicates a pulse of the white light. In a case of FIG. 25B, for example, B and G light are emitted together with the "excitation light". As described above, the control device 12 has a fluorescence imaging mode for performing control to cause the excitation light and the white light to be periodically emitted at the predetermined pulse widths tw-n and tw-w, and to cause, for example, light in at least part of the wavelength bands of the white light, for example, light of the G component and the B component, to be emitted even during the emission period of the excitation light.

The B light and the G light are transmitted through the optical element 56 and received by the second imaging element 52*b*. As a result, the visible image is continuously captured. Furthermore, even if the pulsed light for fluorescence imaging illustrated in FIGS. 25A and 25B is erroneously sent to the ring light 19, it appears to human eyes that white light is continuously emitted, and flickering is reduced. Note that color balance of illumination can be changed by putting a physical optical filter in any place from the light source device 13 to the lens unit 44. Alternatively, in a case of a light source that implements white color illumination by combining light sources having a plurality of wavelengths like RGB-LED, it is possible to change an output of the light source having part of the wavelengths. Note that the white light to be emitted even during the emission period of the excitation light is not limited to the G component and the B component.

As described above, the white light and the narrow band light component (for example, the fluorescence component) are separated into the wavelength separation optical element 56, so that it is also possible to continue to constantly emit the white light as the observation light L1. In other words, it is only necessary to set a difference between the wavelength band and the light emission intensity of the visible light irradiated with the pulse width tw-n, and the wavelength band and the light emission intensity of the visible light irradiated with the pulse width tw-w, within a range in which flickering is not felt by human eyes.

Fifth Embodiment

The observation system 10 according to a fifth embodiment is different from the observation system 10 according to the first embodiment in that the observation system 10 is activated in the second mode. Hereinafter, differences from the observation system 10 according to the first embodiment will be described.

Figure 26:
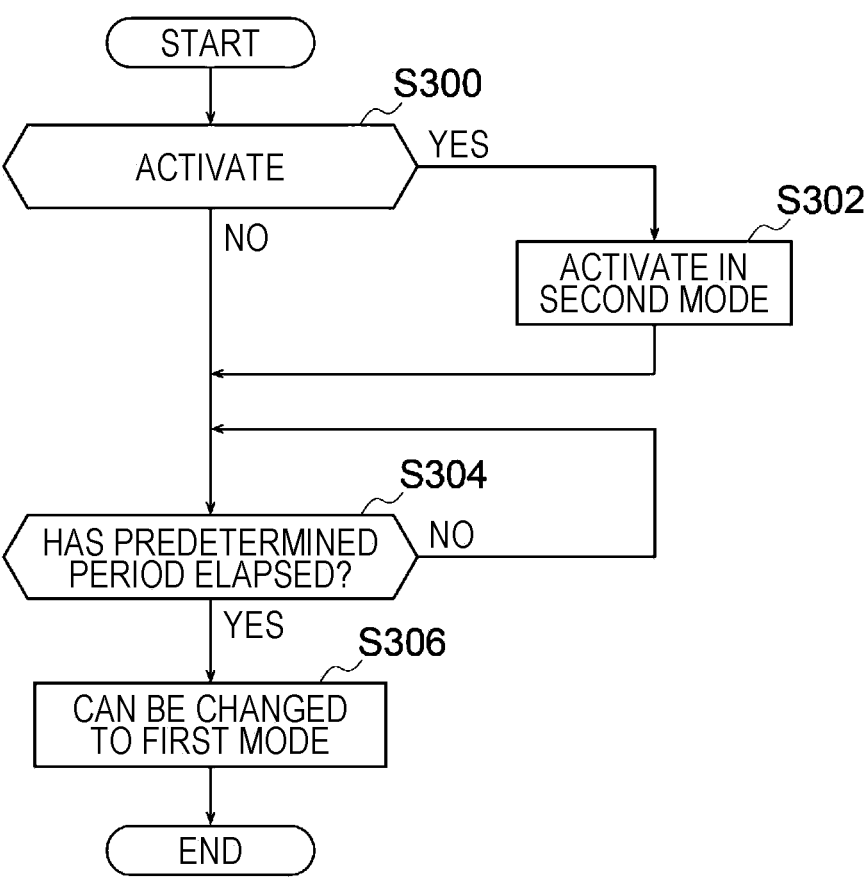
FIG. 26 is a flowchart indicating a processing example at the time of activation.

FIG. 26 is a flowchart indicating a processing example at the time of activation. As indicated in FIG. 26, the control unit 60 determines whether or not it is at the time of activation (step S300). In a case where it is at the time of activation, the control unit 60 selects the second mode and performs activation (step S302).

Next, the control unit 60 determines whether or not a predetermined period has elapsed (step S304). In a case where it is determined that the predetermined period has elapsed (step S304: Y), the control unit 60 accepts the first mode and ends the processing. On the other hand, in a case where the control unit 60 determines that the predetermined period has not elapsed, the control unit 60 repeats the processing of step S304.

In the second mode, light that causes flickering that can be sensed by human eyes is not emitted, and thus, activation is constantly performed in that state. In addition, in a case where the acquisition unit 64 determines that the information on an open field is not included, the control unit 60 displays the software key 510 for selecting the first mode and grays out the software key 512 for selecting the second mode so as not to allow selection (see FIGS. 23A and 23B). In order to enable the first mode in this manner, for example, a condition that a certain period elapses after the activation may be applied. This is because it is assumed that fluorescence observation is often used immediately after activation in applications outside the body cavity. As described above, control of the applications outside the body cavity does not emit light that causes flickering that can be sensed by human eyes, so that it is possible to prevent occurrence of flickering that can be sensed by human eyes by constantly performing activation in that state.

Sixth Embodiment

The observation system 10 according to a sixth embodiment is different from the observation system 10 according to the first embodiment in that, in a case where the ring light 19 is connected to the light source device 13, as well as irradiation that causes flickering that is perceivable by human eyes being not performed, irradiation that causes flickering that is not perceivable by human eyes but affects humans is not performed. Hereinafter, differences from the observation system 10 according to the first embodiment will be described.

Lighting equipment using LED light sources is in general use. The LED light source is often used for blinking control, and thus, standards for blinking of lighting equipment are established. In the observation system 10 according to the sixth embodiment is different from the observation system 10 according to the first embodiment in that the observation system 10 according to the sixth embodiment is capable of conforming to the standards for blinking of general lighting equipment.

As standards of a blinking frequency of such general lighting equipment, international standards (for example, IEEE1789) define that "a blinking frequency equal to or higher than 1.2 kHz and less than 3 kHz has a low risk, and a blinking frequency equal to or higher than 3 kHz has no risk". Further, the Electrical Appliances and Materials Safety Act (PSE Act) of Japan defines that a blinking frequency "equal to or higher than 500 Hz" has no risk. Furthermore, the American Electrical Manufacturers Association (NEMA77 (2017)) defines that a blinking frequency "equal to or higher than 400 Hz" has no risk. As described above, the standards of a blinking frequency "X" Hz of general lighting equipment varies depending on a region, standards to be complied with, or the like. Note that these criteria are criteria for general lighting equipment, and are different from criteria for medical equipment.

The observation system 10 according to the present embodiment prohibits light emission in which a plurality of light emission states which is different in at least one of brightness or a wavelength is switched at a frequency equal to or higher than 3 Hz and less than "X" Hz. In other words, in the observation system 10 according to the present embodiment, a light emission cycle (cycle in which a drive pulse is turned on) of the light source device 13 is adjusted so as to prevent light emission that causes flickering that is perceivable by human eyes and light emission that causes flickering that is not perceivable by human eyes but affects humans. The "X" Hz is, for example, 400 Hz, 500 Hz, 2 kHz to 3 kHz, or the like, and can be made different depending on a region, standards to be complied with, or the like.

In other words, in the observation system 10 according to the present embodiment, it is possible to disable light emission that causes flickering that is perceivable by human eyes and light emission that causes flickering that is not perceivable by human eyes but affects humans. For example, in the observation system 10 according to the present embodiment, it is possible to disable light emission in which a plurality of light emission states which is different in at least one of brightness or a wavelength is temporally switched at a frequency equal to or higher than 3 Hz and less than "X" Hz that is a predetermined value. The "X" Hz is a frequency that can be determined based on a region in which the observation system 10 is to be used.

[Third Light Emission Adjustment Example Regarding Ring Light]

While the target light emission amount of the light source device 13 is relatively large (for example, in a case of INDEX from "17" to "9"), the current value to be supplied to the light source is adjusted and the light emission amount itself from the light source is adjusted in a similar manner to the light emission control related to the rigid endoscope 18 described above (see FIG. 17). On the other hand, in a case where the target light emission amount of the light source device 13 is relatively small (for example, in a case of INDEX from "8" to "1"), the light emission cycle (the cycle in which the drive pulse is ON) is adjusted in addition to the pulse modulation control (PWM control) of the current drive pulse to be supplied to the light source (see FIG. 17).

In other words, light emission (drive pulse-ON) and non-light emission (drive pulse-OFF) are periodically repeated in the light emission control (pulse modulation control) regarding the ring light 19 in a similar manner to the PWM control related to the rigid endoscope 18 according to the second embodiment. However, the light emission control (pulse modulation control) related to the ring light 19 is different from the PWM control related to the rigid endoscope 18 described above in that the light emission frequency is set on the basis of the frequency "X" Hz. In other words, the light emission cycle TL (see (b) of FIG. 17) of the light source device 13 is set so that a value obtained by dividing the cycle TR by the light emission cycle TL and multiplying the result by the frequency of the cycle TR becomes equal to or higher than the frequency "X" Hz. In this manner, the light emission cycle TL is set such that TL<1/X (s). Referring again to (b) of FIG. 18, in a case where the first state (tp period) and the second state (tw period) in which the light emission intensity in a band of visible light is higher than that in the first state are periodically repeated, the light emission is disabled in a case where a repetition cycle is equal to or higher than 3 Hz and less than "X" Hz.

Further, as described above, in a case where the first state (tp period) and the second state (tw period) in which light emission intensity in a band of visible light is higher than that in the first state are periodically repeated, a length of the tw period in the second state also becomes a factor that causes people to feel flickering. For example, as described above, a period of one cycle at a frequency of 65 Hz is about 15.4 ms, and the half cycle is about 7.7 ms. In a visual psychological experiment, if the tw period of the second state is equal to or shorter than 7.7 ms, the state is not recognized, and thus, there is no problem of botheration.

The tw period of the second state described above is about 7.7 ms (=(500/65) ms). Thus, in the observation system 10 according to the present embodiment, the tw period is set so as to be less than the tw period=(500/65) (ms)×(65 (Hz)/X (Hz))=500/X (ms). In other words, in a case where the tw period≥500/X (ms), the light emission is disabled.

For example, in the tw period at 60 Hz, the tw period≥500/60 (ms) is about 8.3 ms. Thus, at a duty ratio of 50%, blinking is switched every about 8.3 ms, and flickering is recognized. Such light emission is disabled. On the other hand, if one cycle of 60 Hz is about 16.7 ms and the duty ratio is 40%:60%, the tw period of the second state and the first state (tp period) become 6.7 ms:10 ms, and the period of 6.7 ms is in an unrecognized region, so that flickering is not felt by human eyes even at 60 Hz. Such light emission can be used without being disabled.

As described above, in a case where the target light emission amount of the light source device 13 is relatively small (for example, in the case of INDEX "8" to "1"), light emission that causes flickering that is perceivable by human eyes and light emission that causes flickering that is not perceivable by human eyes but affects humans are disabled. In other words, light emission in which a plurality of light emission states which is different in at least one of brightness or a wavelength is temporally switched at a frequency equal to or higher than 3 Hz and less than "X Hz" which is a predetermined value is disabled. As described above, the "X" Hz is a frequency that can be determined on the basis of the region in which the observation system is to be used. In addition, in a case where the first state (tp period) and the second state (tw period) in which the emission intensity in a band of visible light is higher than that in the first state are periodically repeated, and the second state (tw period) is maintained for a period longer than Y (ms), the light emission is disabled. Y (ms) at this time is a value obtained by dividing 500 by "X" Hz.

In a case where the light emission is disabled, for example, in a case where manual adjustment is performed by the operator (user) via the software keys 500, 502 (see FIG. 7), the light emission is limited to the range of INDEX "17" to "9". This disables light emission that causes flickering that is perceivable by human eyes and light emission ranges (INDEX "8" to "1") that cause flickering that is not perceivable by human eyes but affects humans.

As described above, according to the present embodiment, in a case where pulse modulation control using pulsed light is used for the ring light 19, the range associated with the target value of a frequency even in the same range of INDEX [8] to [1] as that for the rigid endoscope 18 is set to a range that does not cause flickering that is not perceivable by human eyes but affects humans, in addition to the range that does not cause flickering that is perceivable by human eyes. As a result, it is possible to prevent the irradiation light emitted from the ring light 19 from causing flickering in a situation where the irradiation light enters the eyes of the surgeon, or the like, and to prevent occurrence of flickering that is not perceivable by the human eyes but affects the human.

It should be noted that the embodiments and modifications disclosed herein are illustrative only in all respects and are not to be construed as limiting. The above-described embodiments and modifications can be omitted, replaced, and changed in various forms without departing from the scope and spirit of the appended claims. For example, the above-described embodiments and modifications may be combined in whole or in part, and embodiments other than the above-described embodiments and modifications may be combined with the above-described embodiments or modifications. Furthermore, the effects of the present disclosure described in the present specification are merely examples, and other effects may be provided.

The technical category embodying the above technical idea is not limited. For example, the above-described technical idea may be embodied by a computer program for causing a computer to execute one or a plurality of kinds of procedure (steps) included in a method of manufacturing or using the above-described device. In addition, the above-described technical idea may be embodied by a computer-readable non-transitory recording medium in which such a computer program is recorded.

Note that the present technology can have the following configurations.

(1)

An observation system including a control device that controls irradiation light with which different irradiation environments are irradiated, in which the control device includes:

a control unit that controls a light source device that generates the irradiation light; and an acquisition unit that acquires irradiation environment information regarding an irradiation environment of the irradiation light, the control unit causes a display unit to display a first software key in a case where the irradiation environment information acquired by the acquisition unit includes an open field, and causes the display unit to display a second software key in a case where the irradiation environment information does not include an open field, and a function corresponding to predetermined light emission is disabled in the first software key, and the function corresponding to the predetermined light emission is enabled in the second software key.

(2)

The observation system according to (1), in which the predetermined light emission is light emission that causes flickering that can be sensed by human eyes.

(3)

The observation system according to (1) or (2), in which the predetermined light emission is light emission in which a plurality of light emission states which is different in at least one of brightness or wavelength is temporally switched at a frequency equal to or higher than 3 Hz and less than 65 Hz.

(4)

The observation system according to any one of (1) to (3), in which the predetermined light emission is light emission in which at least a first state and a second state in which light emission intensity in a band of visible light is higher than that in the first state are periodically repeated, and the second state is a period longer than 7.7 ms.

(5)

The observation system according to any one of (1) to (4), in which the software key to be disabled and the software key to be enabled are displayed in different display modes on the display unit.

(6)

The observation system according to any one of (1) to (5), in which the first software key and the second software key are software keys related to brightness control and are associated with target values of brightness.

(7)

The observation system according to (6), in which a range of brightness selectable by the second software key is wider than a range of brightness selectable by the first software key.

(8)

The observation system according to (7), in which a range of a target value of brightness selectable by a user changes between the first software key and the second software key.

(9)

The observation system according to (1), in which the first software key and the second software key are associated with an observation mode selection function.

(10)

The observation system according to any one of (1) to (9), in which the first software key and the second software key are a function for selecting a fluorescence wavelength or an excitation wavelength.

(11)

The observation system according to (10), in which a function corresponding to light emission of visible light is disabled in the first software key, and the function corresponding to the light emission of the visible light is enabled in the second software key.

(12)

The observation system according to any one of (1) to (11), in which the acquisition unit acquires a type of a light guide unit connected to the light source device as irradiation environment information and determines that an open field is included in a case where the light source device is connected via a first-type light guide unit, and determines that the open field is not included in a case where the light source device is connected via a second-type light guide unit different from the first-type light guide unit.

(13)

The observation system according to any one of (1) to (11), in which the acquisition unit acquires a captured image output from an imaging device that captures an image of light from a subject as the irradiation environment information and determines whether or not the open field is included on the basis of the captured image.

(14)

The observation system according to (13), in which the acquisition unit has a recognition function of recognizing a category of the captured image, and the acquisition unit determines whether or not the open field is included on the basis of the category.

(15)

The observation system according to any one of (1) to (11), in which an illumination device for image observation in a state of being attached to an imaging device causes the imaging device to receive light from a subject while shielding part of the light in a form different from that of an illumination device for open field in a state of being attached to the imaging device, and the acquisition unit acquires information on a light shielding portion in a captured image output from the imaging device as the irradiation environment information and determines whether or not the open field is included on the basis of the information on the light shielding portion.

(16)

The observation system according to any one of (1) to (11), in which the acquisition unit acquires information as to whether or not an illumination device for image observation has passed through a trocar as the irradiation environment information and determines whether or not the open field is included on the basis of the information as to whether or not the illumination device for image observation has passed through the trocar.

(17)

The observation system according to any one of (1) to (16), in which the first software key is displayed on the display unit upon activation of the control device.

(18)

The observation system according to any one of (1) to (17), further including:

the light source device connectable to an illumination device for image observation and an illumination device for open field; and an imaging device connectable to the illumination device for image observation and the illumination device for open field.

(19)

The observation system according to (1), in which in a case where an imaging device connected to the control device includes a first imaging element that receives white light and a second imaging element that receives narrow band light corresponding to excitation light, the observation system has a mode in which the control device executes control of causing the light source device to periodically emit the excitation light and the white light at predetermined intervals and causing the light source device to emit light in at least part of a wavelength band of the white light also during a light emission period of the excitation light.

(20)

A light emitting method for emitting irradiation light with which different irradiation environments are irradiated, the light emitting method including:

acquiring an information signal including irradiation environment information regarding an irradiation environment of the irradiation light;

determining whether or not the irradiation environment information includes an open field by the information signal; and causing a display unit to display a first software key by a control signal in a case where the irradiation environment information includes the open field, and causing the display unit to display a second software key by the control signal in a case where the irradiation environment information does not include the open field, in which a function corresponding to predetermined light emission is disabled in the first software key, and the function corresponding to the predetermined light emission is enabled in the second software key.

(21)

An observation system including a control device that controls irradiation light with which different irradiation environments are irradiated, in which the control device includes:

a control unit that controls a light source device that generates the irradiation light; and an acquisition unit that acquires irradiation environment information regarding an irradiation environment of the irradiation light, the control unit causes a display unit to display a first software key in a case where the irradiation environment information acquired by the acquisition unit includes an open field, and causes the display unit to display a second software key in a case where the irradiation environment information does not include an open field, the first software key has a function of periodically repeating at least a first state and a second state in which light emission intensity in a band of visible light is higher than that in the first state, and has a limitation in a function for a frequency for light emission in which the second state has a period longer than 7.7 ms, and the second software key does not have the limitation in the function for the frequency.

(22)

A control device that controls irradiation light with which different irradiation environments are irradiated, the control device including:

a control unit that controls a light source device that generates the irradiation light; and an acquisition unit that acquires irradiation environment information regarding an irradiation environment of the irradiation light, in which the control unit causes a display unit to display a first software key in a case where the irradiation environment information acquired by the acquisition unit includes an open field, and causes the display unit to display a second software key in a case where the irradiation environment information does not include the open field, and a function corresponding to predetermined light emission is disabled in the first software key, and a function corresponding to the predetermined light emission is enabled in the second software key.

(23)

The observation system according to (1), in which the predetermined light emission is at least one of light emission that causes flickering that is perceivable by human eyes or light emission that causes flickering that is not perceivable by human eyes but affects humans.

(24)

The observation system according to (1) in which the predetermined light emission is light emission in which a plurality of light emission states which is different in at least one of brightness or a wavelength is temporally switched at a frequency equal to or higher than 3 Hz and less than X Hz which is a predetermined value, and the X Hz is a frequency that can be determined on the basis of a region in which the observation system is to be used.

(25)

The observation system according to (24), in which the predetermined light emission is light emission in which at least a first state and a second state in which light emission intensity in a band of visible light is higher than that in the first state are periodically repeated, and the second state is maintained for a period longer than Y ms, and the Y ms is a value obtained by dividing 500 by the X Hz.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

10 Observation system
11 Imaging device
12 Control device
13 Light source device
14 Display device
16 Light guide
16a First light guide end portion
16b Second light guide end portion
18 Rigid endoscope
19 Ring light
20 Insertion portion
21 Insertion distal end portion
22 Optical connection portion
23 Imaging connection portion
32 Light guide
33 Imaging connection portion
45 Connector
52 Imaging element
52a First imaging element
52b Second imaging element
56 Wavelength separation optical element

60 Control unit
61 Communication unit
62 Image generation unit
64 Acquisition unit
65 Touch panel
90 Subject
500 Software key
502 Software key
510 Software key
512 Software key
L1 Observation light
TL Light emission cycle
TR Exposure cycle
tp Inter-pulse interval
tw Pulse width
P Captured image
P0 Observation image
P1 Light shielding portion

The invention claimed is:

1. An observation system comprising a control device that controls irradiation light with which different irradiation environments are irradiated, wherein
the control device includes:
a control unit that controls a light source device that generates the irradiation light; and
an acquisition unit that acquires irradiation environment information regarding an irradiation environment of the irradiation light,
the control unit causes a display unit to display a first software key in a case where the irradiation environment information acquired by the acquisition unit includes an open field, and causes the display unit to display a second software key in a case where the irradiation environment information does not include an open field, and
a function corresponding to predetermined light emission is disabled in the first software key, and the function corresponding to the predetermined light emission is enabled in the second software key.

2. The observation system according to claim 1, wherein the predetermined light emission includes light emission that causes flickering that can be sensed by human eyes.

3. The observation system according to claim 1, wherein the predetermined light emission includes light emission in which a plurality of light emission states which is different in at least one of brightness or wavelength is temporally switched at a frequency equal to or higher than 3 Hz and less than 65 Hz.

4. The observation system according to claim 1, wherein the predetermined light emission includes light emission in which at least a first state and a second state in which light emission intensity in a band of visible light is higher than that in the first state are periodically repeated, and the second state is maintained for a period longer than 7.7 ms.

5. The observation system according to claim 1, wherein the software key to be disabled and the software key to be enabled are displayed in different display modes on the display unit.

6. The observation system according to claim 1, wherein the first software key and the second software key include software keys related to brightness control and are associated with target values of brightness.

7. The observation system according to claim 6, wherein a range of brightness selectable by the second software key is wider than a range of brightness selectable by the first software key.

8. The observation system according to claim 7, wherein a range of a target value of brightness selectable by a user changes between the first software key and the second software key.

9. The observation system according to claim 1, wherein the first software key and the second software key are associated with an observation mode selection function.

10. The observation system according to claim 1, wherein the first software key and the second software key are associated with a function for selecting a fluorescence wavelength or an excitation wavelength.

11. The observation system according to claim 10, wherein a function corresponding to light emission of visible light is disabled in the first software key, and the function corresponding to the light emission of the visible light is enabled in the second software key.

12. The observation system according to claim 1, wherein
the acquisition unit acquires a type of a light guide unit connected to the light source device as the irradiation environment information and determines that an open field is included in a case where the light source device is connected via a first-type light guide unit, and
determines that the open field is not included in a case where the light source device is connected via a second-type light guide unit different from the first-type light guide unit.

13. The observation system according to claim 1, wherein the acquisition unit acquires a captured image output from an imaging device that captures an image of light from a subject as the irradiation environment information and determines whether or not the open field is included on a basis of the captured image.

14. The observation system according to claim 13, wherein
the acquisition unit has a recognition function of recognizing a category of the captured image, and
the acquisition unit determines whether or not the open field is included on a basis of the category.

15. The observation system according to claim 1, wherein
an illumination device for image observation in a state of being attached to an imaging device causes the imaging device to receive light from a subject while shielding part of the light in a form different from that of an illumination device for open field in a state of being attached to the imaging device, and
the acquisition unit acquires information on a light shielding portion in a captured image output from the imaging device as the irradiation environment information and determines whether or not the open field is included on a basis of the information on the light shielding portion.

16. The observation system according to claim 1, wherein the acquisition unit acquires information as to whether or not at least part of an illumination device for image observation has passed through a trocar as the irradiation environment information and determines whether or not the open field is included on a basis of the information as to whether or not at least part of the illumination device for image observation has passed through the trocar.

17. The observation system according to claim 1, wherein the first software key is displayed on the display unit upon activation of the control device.

18. The observation system according to claim 1, further comprising:
the light source device connectable to an illumination device for image observation and an illumination device for open field; and an imaging device connectable to the illumination device for image observation and the illumination device for open field.

19. The observation system according to claim 1, wherein in a case where an imaging device connected to the control device includes a first imaging element that receives white light and a second imaging element that receives fluorescence generated by excitation light, the observation system has a fluorescence imaging mode in which the control device executes control of causing the light source device to periodically emit the excitation light and the white light at predetermined intervals and causing the light source device to emit light in at least part of a wavelength band of the white light also during a light emission period of the excitation light.

20. A light emitting method for emitting irradiation light with which different irradiation environments are irradiated, the light emitting method comprising:

acquiring an information signal including irradiation environment information regarding an irradiation environment of the irradiation light;

determining whether or not the irradiation environment information includes an open field by the information signal; and causing a display unit to display a first software key by a control signal in a case where the irradiation environment information includes the open field, and causing the display unit to display a second software key by the control signal in a case where the irradiation environment information does not include the open field, wherein a function corresponding to predetermined light emission is disabled in the first software key, and the function corresponding to the predetermined light emission is enabled in the second software key.

21. An observation system comprising a control device that controls irradiation light with which different irradiation environments are irradiated, wherein the control device includes:

a control unit that controls a light source device that generates the irradiation light; and an acquisition unit that acquires irradiation environment information regarding an irradiation environment of the irradiation light, the control unit causes a display unit to display a first software key in a case where the irradiation environment information acquired by the acquisition unit includes an open field, and causes the display unit to display a second software key in a case where the irradiation environment information does not include an open field, the first software key corresponds to a function of periodically repeating at least a first state and a second state in which light emission intensity in a band of visible light is higher than that in the first state, and has a limitation such that the second state is light emission of a period longer than 7.7 ms, and the second software key does not have the limitation.

22. The observation system according to claim 1, wherein the predetermined light emission includes light emission that causes flickering that is perceivable by human eyes and light emission that causes flickering that is not perceivable by human eyes but affects humans.

23. The observation system according to claim 1, wherein the predetermined light emission includes light emission in which a plurality of light emission states which is different in at least one of brightness or a wavelength is temporally switched at a frequency equal to or higher than 3 Hz and less than X Hz which is a predetermined value, and the X Hz is a frequency that can be determined on a basis of a region in which the observation system is to be used.

24. The observation system according to claim 23, wherein the predetermined light emission includes light emission in which at least a first state and a second state in which light emission intensity in a band of visible light is higher than that in the first state are periodically repeated, and the second state is maintained for a period longer than Y ms, and the Y ms is a value obtained by dividing 500 by the X Hz.

* * * * *